US008435488B2

(12) United States Patent
Gill et al.

(10) Patent No.: US 8,435,488 B2
(45) Date of Patent: May 7, 2013

(54) METHODS AND COMPOSITIONS FOR PROTEIN LABELLING

(75) Inventors: Herman Gill, San Mateo, CA (US); Jan Marik, Hillsborough, CA (US); Jeff Tinianow, San Francisco, CA (US); Simon Williams, Redwood City, CA (US)

(73) Assignee: Genentech, Inc., South San Francisco, CA (US)

( * ) Notice: Subject to any disclaimer, the term of this patent is extended or adjusted under 35 U.S.C. 154(b) by 436 days.

(21) Appl. No.: 12/712,285

(22) Filed: Feb. 25, 2010
(Under 37 CFR 1.47)

(65) Prior Publication Data

US 2010/0221176 A1 Sep. 2, 2010

Related U.S. Application Data

(60) Provisional application No. 61/156,165, filed on Feb. 27, 2009.

(51) Int. Cl.
*A61K 51/00* (2006.01)
*A61M 36/14* (2006.01)

(52) U.S. Cl.
USPC ........ 424/1.11; 424/1.41; 424/1.49; 530/351; 530/391.3; 530/399; 530/409; 800/3

(58) Field of Classification Search .................. None
See application file for complete search history.

(56) References Cited

U.S. PATENT DOCUMENTS

| | | | |
|---|---|---|---|
| 7,375,234 | B2 | 5/2008 | Sharpless et al. |
| 7,521,541 | B2 | 4/2009 | Eigenbrot et al. |
| 2006/0263293 | A1 | 11/2006 | Kolb et al. |
| 2006/0269942 | A1 | 11/2006 | Kolb et al. |
| 2008/0161537 | A1 | 7/2008 | Padilla De Jesus et al. |
| 2008/0170992 | A1 | 7/2008 | Kolb et al. |
| 2008/0311412 | A1 | 12/2008 | Fokin et al. |
| 2010/0111856 | A1 | 5/2010 | Gill et al. |

FOREIGN PATENT DOCUMENTS

| WO | WO 2006067376 A2 | * | 6/2006 |
|---|---|---|---|
| WO | WO 2007127473 A2 | * | 11/2007 |

OTHER PUBLICATIONS

"International Search Report in PCT/US2010/025334".
Berndt et al., "Labeling of low density lipoproteins using the $^{18}$F-labeled thiol-reactive reagent N-[6-(4-[$^{18}$F] fluorobenzylidene)aminooxyhexyl]maleimide" *Nucl. Med. Biol.* 34:5-15 (2007).
Boswell et al., "Development of radioimmunotherapeutic and diagnostic antibodies: an inside-out view" *Nucl. Med. and Biol.* 34:757-778 (2007).
Cai at al., "A Thiol Reactive $^{18}$F-Labeling Agent, N-[2-(4-$^{18}$F-Fluorobenzamido)Ethyl]Maleimide, and Synthesis of RGD Peptide-Based Tracer for PET Imaging of $\alpha_v\beta_3$ Integrin Expression" *J. Nucl. Med.* 47:1172-1180 (2006).
de Bruin et al., "1-[3-(2-[$^{18}$F]Fluoropyridin-3-yloxy)propyl]pyrrole-2,5-dione: Design, Synthesis, and Radiosynthesis of a New [$^{18}$F]Fluoropyridine-Based Maleimide Reagent for the Labeling of Peptides and Proteins" *Bioconjugate Chem.* 16:406-420 (2005).
Devaraj et al., "$^{18}$F labeled nanoparticles for in vivo PET-CT imaging" *Bioconjugate Chem.* 20:397-401 (2009).
Gill et al., "A Modular Platform for the Rapid Site-Specific Radiolabeling of Proteins with $^{18}$F Exemplified by Quantitative Positron Emission Tomography of Human Epidermal Growth Factor Receptor 2" *Journal of Medicinal Chemistry* 52:5816-5825 (2009).
Glaser et al., "Click Labeling with 2-[$^{18}$F]fluoroethylazide for positron emission tomography" *Bioconjugate Chem.* 18:989-993 (2007).
Glaser et al., "Methods for $^{18}$F-labeling of RGD peptides: comparison of aminooxy [$^{18}$F]fluorobenzaldehyde condensation with 'click labeling' using 2-[$^{18}$F]fluoroethylazide, and S-alkylation with [$^{18}$F]fluoropropanethiol" *Amino Acids* 37(4):717-724 (2008).
Hausner at al., "In vivo positron emission tomography (PET) imaging with an $\alpha_v\beta_6$ specific peptide radiolabeled using $^{18}$F-"click" chemistry: evaluation and comparison with the corresponding 4-[$^{18}$F]fluorobenzoyl- and 2-[$^{18}$F]fluoropropionyl-peptides" J. Med. Chem. 51:5901-5904 (2008).
Hausner at al., "Targeted In vivo Imaging of Integrin $\alpha_v\beta_6$ with an Improved Radiotracer and Its Relevance in a Pancreatic Tumor Model" *Cancer Research* 69(14):5843-5850 (Jul. 2009).

(Continued)

*Primary Examiner* — Michael G Hartley
*Assistant Examiner* — Sean R Donohue
(74) *Attorney, Agent, or Firm* — Alex Andrus; Genentech, Inc.

(57) ABSTRACT

A modular platform is provided for rapid preparation of various water-soluble prosthetic groups capable to efficiently introduce $^{18}$F into proteins with $^{18}$F labelling reagents.

5 Claims, 3 Drawing Sheets

OTHER PUBLICATIONS

Hausner et al., "Use of a Peptide Derived from Foot-and-Mouth Disease Virus for the Noninvasive Imaging of Human Cancer: Generation and Evaluation of 4-[$^{18}$F]Fluorobenzoyl A20FMDV2 for In vivo Imaging of Integrin $\alpha\nu\beta_6$ Expression with Positron Emission Tomography" Cancer Research 67(16):7833-7840 (Aug 2007).

Inkster at al., "Radiosynthesis and bioconjugation of [$^{18}$F]FPy5yne, a prosthetic group for the $^{18}$F labelling of bioactive peptides" *Journal of Labelled Compounds and Radiopharmaceuticals* 51:444-452 (2008).

Junutula at al., "Rapid identification of reactive cysteine residues for site-specfic labeling of antibody-Fabs" *J Immunol Methods* 332:41-52 (2008).

Junutula et al., "Site-specific conjugation of a cytotoxic drug to an antibody improves the therapeutic index" *Nat Biotechnol.* 26(8):925-32 (Aug. 2008).

Lahorte et al., "Apoptosis-detecting radioligands: current state of the art and future perspectives" *European Journal of Nuclear Medicine and Molecular Imaging* 31(6):887-919 (2004).

Li et al., "Click chemistry for $^{18}$F-labeling of RGD peptides and microPET imaging of tumor integrin $\alpha_\nu\beta_3$ expression" *Bioconjugate Chem.* 18:1987-1994 (2007).

Li et al., "Site-specific Labeling of Annexin V with F-18 for Apoptosis Imaging" *Bioconjugate Chem.* 19:1684-1688 (2008).

Lu et al., "An iterative route to "decorated" ethylene glycol-based linkers" *Chemical Communications* pp. 1652-1654 (2006).

Marik et al., "Click for PET: rapid preparation of [$^{18}$F]fluoropeptides using Cu$^1$ catalyzed 1,3-dipolar cycloaddition" *Tetrahedron Letters* 47:6681-6684 (2006).

Marik et al., "Fully automated preparation of n.c.a. 4-[$^{18}$F]fluorobenzoic acid and N-succinimidyl 4-[$^{18}$F]fluorobenzoate using a siemens/CTI chemistry process control unit (CPCU)" *Applied Radiation and Isotopes* 65:199-203 (2007).

Marik et al., "Long-circulating liposomes radiolabeled with with [$^{18}$F]fluorodipalmitin ([$^{18}$F]FDP)" *Nuclear Medicine and Biology* 34:165-171 (2007).

Marik et al., "PET of glial metabolism using 2-$^{18}$F-fluoroacetate" *Journal of Nuclear Medicine* 50(6):982-990 (2009).

Marik et al., "Solid-phase synthesis of 2-[$^{18}$F]fluoropropionyl peptides" *Bioconjugate Chem.* 17:1017-1021 (2006).

Okarvi, S.M., "Recent progress in fluorine-18 labelled peptide radiopharmaceuticals" *European Journal of Nuclear Medicine* 27(7):929-938 (2001).

Smith-Jones et al., "Early Tumor Response to Hsp90 Therapy HER2 PET: Comparison with $^{18}$F-FDG PET" *J. Nucl. Med.* 47:793-796 (2006)

Smith-Jones et al., "Imaging the pharmacodynamics of HER2 degradation in response to Hsp90 inhibitors" *Nature Biotechnology* 22:701-706 (2004).

Stephenson et al., "Fluoro-pegylated (FPEG) imaging agents targeting A$\beta$ aggregates" *Bioconjugate Chem.* 18:238-246 (2007).

Tinianow at al., "Site-specifically $^{89}$Zr-labeled Monoclonal Antibodies for ImmunoPET" *Nuclear Medicine and Biology* 37:289-297 (2010)

Toyokuni et al., "Synthesis of a new heterobifunctional linker, N-[4-(aminooxy)butyl]maleimide, for facile access to a thiol-reactive $^{18}$F-labeling agent" *Bioconjugate Chem.* 14:1253-1259 (2003).

Williams et al., "Numerical Selection of Optimal Tumor Imaging Agents with Application to Engineered Antibodies" *Cancer Biotherapy and Radiopharmaceuticals* 16:25-35 (2001).

Wuest at al., "Synthesis and Application of [$^{18}$F]FDG-Maleimidehexyloxime ([$^{18}$F]FDG-MHO): A [$^{18}$F]FDG-Based Prosthetic Group for the Chemoselective $^{18}$F-Labeling of Peptides and Proteins" *Bioconjugate Chem.* 19:1202-1210 (2008).

Wuest et al., "Systematic comparison of two novel, thiol-reactive prosthetic groups for $^{18}$F labeling of peptides and proteins with the acylation agent succinimidyl-4-[18F]fluorobenzoate ([$^{18}$]SFB)" *Amino Acids* 36:283-295 (2009).

* cited by examiner

METHODS AND COMPOSITIONS FOR PROTEIN LABELLING

CROSS REFERENCE TO RELATED APPLICATIONS

This non-provisional application filed under 37 CFR §1.53 (b), claims the benefit under 35 USC §119(e) of U.S. Provisional Application Ser. No. 61/156,165 filed on 27 Feb. 2009, which is incorporated by reference in entirety.

FIELD OF THE INVENTION

The invention relates generally to methods to conjugate or label groups to proteins. The invention also relates to labelled proteins, and intermediates and reagents useful to prepare labelled proteins for research and clinical development of novel therapeutics and diagnostic tests.

BACKGROUND OF THE INVENTION

Proteins and peptides make up a large part of the armamentarium available for the molecular imaging of cell-surface biomarkers. Targeted proteins produced by genetic engineering are very attractive as PET imaging agents, but labeling with conventional $^{18}$F-based prosthetic groups is problematic due to long synthesis times, poor radiochemical yields, and low specific activity. Although the development of "ideal" imaging agents is an important goal, in practice many imaging agents are developed from existing proteins, such as monoclonal antibodies (Mabs) and their engineered fragments, which are initially developed as potential therapeutic agents or to explore a target's biology. PET imaging agents may function in diagnostic assays or biomarker tests, to enable patient selection, inform decisions around indication choice for therapeutic candidates, and maximize clinical benefit of a therapeutic agent that targets the same receptor or disease pathway. Predictive biomarker tests are conducted before treatment to predict whether a particular treatment is likely to be beneficial. Prognostic biomarkers are correlated with disease outcome and may improve clinical trial design and treatment, and data interpretation confidence levels.

The development of Positron Emission Tomographic (PET) imaging agents from a Mab template (Immuno-PET) holds promise as a tool for localizing and quantifying molecular targets and may enhance the non-invasive clinical diagnosis of pathological conditions (van Dongen et al (2007) Oncologist 12; 1379-89; Williams et a (2001) Cancer Biother Radiopharm 16:25-35; Holliger et al (2005) Nat Biotechnol 23:1126-36). PET is a molecular imaging technology that is increasingly used for detection of disease. PET imaging systems create images based on the distribution of positron-emitting isotopes in the tissue of a patient. The isotopes are typically administered to a patient by injection of probe molecules that comprise a positron-emitting isotope, such as F-18, C-11, N-13, or O-15, covalently attached to a molecule that is readily metabolized or localized in the body (e.g., glucose) or that chemically binds to receptor sites within the body. In some cases, the isotope is administered to the patient as an ionic solution or by inhalation. Small immuno-PET imaging agents, such as Fab antibody fragments (50 kDa) or diabodies, paired dimers of the covalently associated $V_H$-$V_L$ region of Mab, 55 kDa (Shively et al (2007) J Nucl Med 48:170-2), may be particularly useful since they exhibit a short circulation half-life, high tissue permeability, and reach an optimal tumor to background ratio between two to four hours after injection facilitating the use of short half-life isotopes such as the widely available $^{18}$F (109.8 min).

Targeted proteins produced by genetic engineering are very attractive as PET imaging agents, but labeling with conventional $^{18}$F-based prosthetic groups is problematic due to long synthesis times, poor radiochemical yields, and low specific activity. a modular platform for rapid preparation of various water-soluble prosthetic groups capable to efficiently introduce $^{18}$F into proteins. Combining the sensitivity and high-resolution offered by $^{18}$F-based PET imaging with the high specificity of these antibody fragments is a particularly attractive strategy for the research and clinical development of novel diagnostic assays and therapeutics. Production of $^{18}$F-labeled proteins by current methods is inadequate because relatively mild aqueous reaction conditions are necessary to preserve the function of most proteins. Existing $^{18}$F-labeled prosthetic groups used for protein conjugations are often limited by some combination of poor radiochemical yield, long synthesis time, and low specific activity. Improved methods for generating $^{18}$F-labeled proteins are valuable in facilitating molecular imaging in humans to address clinical development processes such as level of target expression, heterogeneity and course of expression.

Site-specific conjugation is preferred over random amino modification as it enables chemical modification of a site away from the binding site, promoting complete retention of biological activity and allowing control over the possible number of prosthetic groups added. Genetically engineered proteins containing cysteine at select positions have been investigated for developing site-specific conjugations (Junutula, J. R. et al (2008) J Immunol Methods 332:41-52; US 2007/0092940). The radionuclide labelling of thiol groups on engineered cysteine residues by prosthetic groups is advantageous as a site-specific method since the presence of cysteine is limited within the proteome, of which the non-reactive disulfide form is dominant (Olafsen et al (2004) Protein Eng Des Sel 17:21-7; Tait et al (2006) J Nucl Med 47:1546-53; Li et al (2008) Bioconjug Chem 19:1684-8). A protein engineering method, PHESELECTOR, employs phage display library to select the optimal amino acid position for cysteine substitution (Junutula et al. (2008) Nat Biotechnol 26:925-32; Junutula et al (2008) J Immunol Methods 332:41-52; US 2007/0092940). Using the PHESELECTOR method, protein stability and binding affinity is retained while the formation of undesired disulfide bonds is minimized providing optimal conjugation efficiencies. This method is used to produce modified Mab containing an available cysteine (ThioMab), from which a Fab fragment (ThioFab) with a reactive thiol group is conveniently generated.

Prosthetic groups containing the maleimide group, such as [$^{18}$F]FBEM (Cai et al (2006) J Nucl Med 47:1172-80), [$^{18}$F]FBAM (Berndt et al (2007) Nucl Med Biol 34:5-15), [$^{18}$F]FBABM (Li et al (2008) Bioconjug Chem 19:1684-8; Toyokuni et al (2003) Bioconjug Chem 14:1253-9), [$^{18}$F]FBOM (Wuest et al (2009) Amino Acids 36:283-295), [$^{18}$F]FDG-MHO (Wuest et al (2008) Bioconjug Chem 19:1202-10), and [$^{18}$F]FPyMe (de Bruin et al (2005) Bioconjug Chem 16:406-20), have been used to site-specifically introduce $^{18}$F into a thiol-bearing protein. These labelling reagents [$^{18}$F]FBEM, [$^{18}$F]FBAM, [$^{18}$F]FBABM, and [$^{18}$F]FBOM were developed from a common platform where the aromatic precursor, $^{18}$F-fluorobenzaldehyde ([$^{18}$F]FBALD), is coupled with an aminooxy-bearing maleimide precursor. However, the presence of aromatic and (with the exception of [$^{18}$F]FBOM) aliphatic moieties enhances the lipophilicity of these prosthetic groups, potentially limiting the conjugation efficiency with protein thiol groups present within a hydrophilic environment. Furthermore, these prosthetic groups require long synthesis times and typically provide relatively poor radiochemical yields of $^{18}$F-labeled protein.

SUMMARY

A modular platform is provided for rapid preparation of various water-soluble prosthetic groups capable to efficiently introduce $^{18}$F into proteins.

An aspect of the invention includes methods of labelling a protein comprising reacting a labelling reagent and a protein to form a labelled protein. Labelling reagents include:

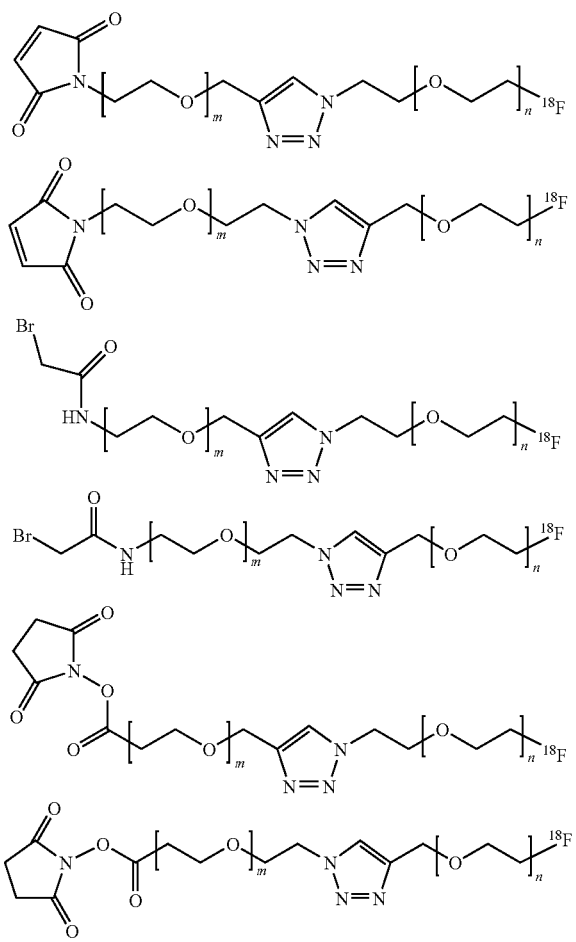

wherein n and m are independently selected from an integer from 2 to 12.

An aspect of the invention includes processes for making a labelling reagent.

An aspect of the invention includes labelled proteins selected from:

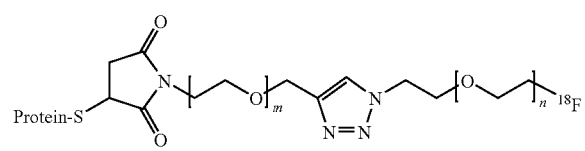

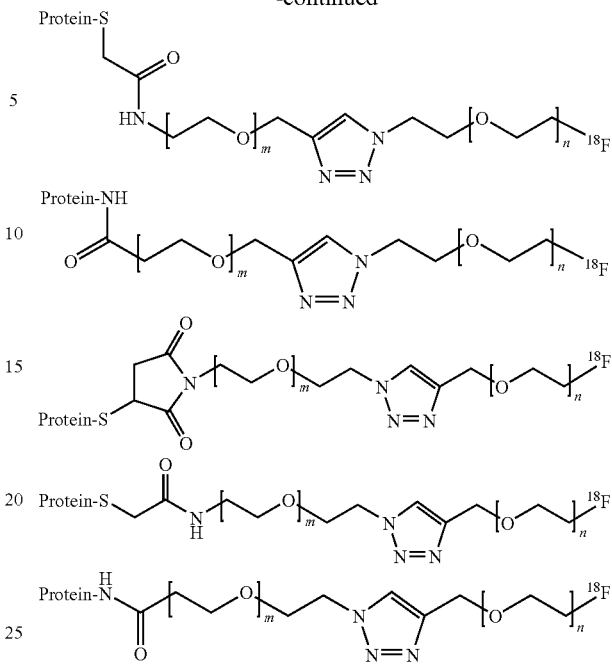

An aspect of the invention includes pharmaceutical compositions comprising a labelled protein and one or more pharmaceutically acceptable carrier, glidant, diluent, or excipient.

An aspect of the invention includes method of imaging comprising administering a labelled protein to an animal; and detecting in vivo the presence of the labelled protein by imaging.

DETAILED DESCRIPTION OF THE EXEMPLARY EMBODIMENTS

Figure 1:
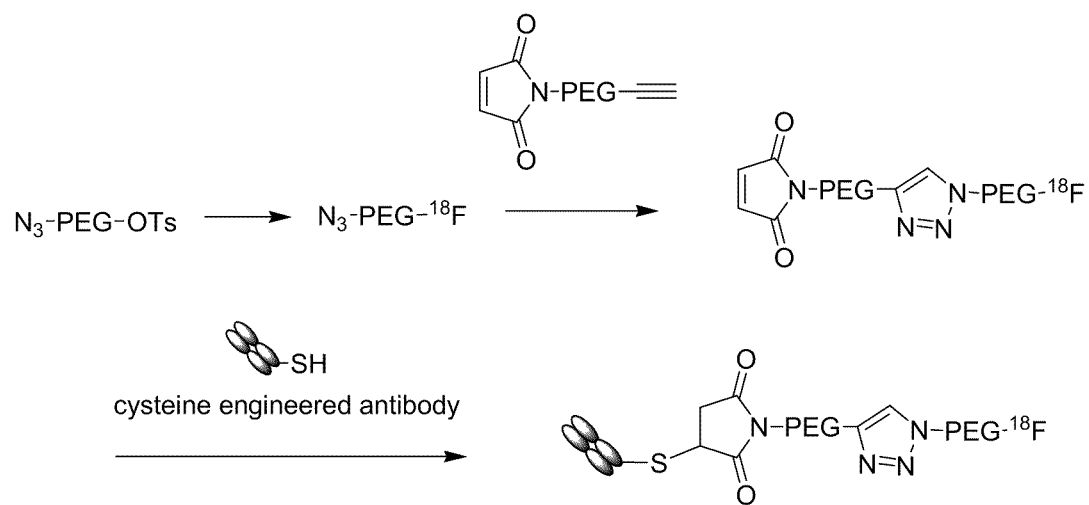
FIG. 1 shows an exemplary synthetic route for radiolabeling Fab fragments using [$^{18}$F]FPEGMA. PEG=2-12 ethyloxy units

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the claims. One skilled in the art will recognize many methods and materials similar or equivalent to those described herein, which could be used in the practice of the present invention. The present invention is in no way limited to the methods and materials described.

Unless defined otherwise, technical and scientific terms used herein have the same meaning as commonly understood by one of ordinary skill in the art to which this invention belongs, and are consistent with: Singleton et al, (1994) "Dictionary of Microbiology and Molecular Biology", 2nd Ed., J. Wiley & Sons, New York, N.Y.; and Janeway, et al (2001) "Immunobiology", 5th Ed., Garland Publishing, New York. When trade names are used herein, applicants intend to independently include the trade name product formulation, the generic drug, and the active pharmaceutical ingredient(s) of the trade name product.

DEFINITIONS

Unless stated otherwise, the following terms and phrases as used herein are intended to have the following meanings:

A "protein" is an organic compound made of amino acids arranged in a linear chain and joined together by peptide bonds between the carboxyl and amino groups of adjacent amino acid residues. Proteins are biological macromolecules and include enzymes and antibodies. Many proteins are vital to metabolism, cell signaling, immune responses, cell adhesion, cell cycle effects, or have structural or mechanical functions, such as in muscle and the cytoskeleton. Functional classes of exemplary proteins include an antibody, a non-antibody alternative binding protein (Binz et al (2005) Nature Biotechnology 23(10):1257-1268; Skerra, A. (2007) Current Opin. in Biotech. 18:295-304), an interferon, a lymphokine, a cytokine, a hormone, or a growth factor "Antibody" is used in the broadest sense and specifically covers monoclonal antibodies, polyclonal antibodies, multi-specific antibodies (e.g., bispecific antibodies), dual-acting Fabs, and other antibody fragments. Antibodies may be murine, human, humanized, chimeric, or derived from other species. An antibody is a protein generated by the immune system that is capable of recognizing and binding to a specific antigen. (Janeway, et al (2001) "Immunobiology", 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody. Antibody also refers to a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. Tumor-associated cell surface antigen polypeptides, i.e. tumor associated antigens (TAA), allows specific targeting of cancer cells for destruction via antibody-based therapies. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule. The immunoglobulins can be derived from any species. In one aspect, however, the immunoglobulin is of human, murine, or rabbit origin.

Therapeutic monoclonal antibodies useful for the methods of the invention include trastuzumab (HERCEPTIN®, Genentech, Inc., Carter et al (1992) Proc. Natl. Acad. Sci. USA, 89:4285-4289; U.S. Pat. No. 5,725,856); anti-CD20 antibodies such as chimeric anti-CD20 "C2B8" (U.S. Pat. No. 5,736,137); rituximab (RITUXAN®), ocrelizumab, a chimeric or humanized variant of the 2H7 antibody (U.S. Pat. No. 5,721,108; WO 04/056312) or tositumomab (BEXXAR®); anti-IL-8 (St John et al (1993) Chest, 103:932, and WO 95/23865); anti-VEGF antibodies including humanized and/or affinity matured anti-VEGF antibodies such as the humanized anti-VEGF antibody huA4.6.1 bevacizumab (AVASTIN®, Genentech, Inc., Kim et al (1992) Growth Factors 7:53-64, WO 96/30046, WO 98/45331); anti-PSCA antibodies (WO 01/40309); anti-CD40 antibodies, including S2C6 and humanized variants thereof (WO 00/75348); anti-CD11a (U.S. Pat. No. 5,622,700; WO 98/23761; Steppe et al (1991) Transplant Intl. 4:3-7; Hourmant et al (1994) Transplantation 58:377-380); anti-IgE (Presta et al (1993) J. Immunol. 151:2623-2632; WO 95/19181); anti-CD18 (U.S. Pat. No. 5,622,700; WO 97/26912); anti-IgE, including E25, E26 and E27 (U.S. Pat. No. 5,714,338; U.S. Pat. No. 5,091,313; WO 93/04173; U.S. Pat. No. 5,714,338); anti-Apo-2 receptor antibody (WO 98/51793); anti-TNF-alpha antibodies including cA2 (REMICADE®), CDP571 and MAK-195 (U.S. Pat. No. 5,672,347; Lorenz et al (1996) J. Immunol. 156(4):1646-1653; Dhainaut et al (1995) Crit. Care Med. 23(9):1461-1469); anti-Tissue Factor (TF) (EP 0 420 937 B1); anti-human alpha 4 beta 7 integrin (WO 98/06248); anti-EGFR, chimerized or humanized 225 antibody (WO 96/40210); anti-CD3 antibodies such as OKT3 (U.S. Pat. No. 4,515,893); anti-CD25 or anti-tac antibodies such as CHI-621 SIMULECT® and ZENAPAX® (U.S. Pat. No. 5,693,762); anti-CD4 antibodies such as the cM-7412 antibody (Choy et al (1996) Arthritis Rheum 39(1):52-56); anti-CD52 antibodies such as CAMPATH-1H (Riechmann et al (1988) Nature 332:323-337); anti-Fc receptor antibodies such as the M22 antibody directed against Fc gamma RI as in Graziano et al (1995) J. Immunol. 155(10):4996-5002; anti-carcinoembryonic antigen (CEA) antibodies such as hMN-14 (Sharkey et al (1995) Cancer Res. 55(23Suppl): 5935s-5945s; antibodies directed against breast epithelial cells including huBrE-3, hu-Mc 3 and CHL6 (Ceriani et al (1995) Cancer Res. 55(23): 5852s-5856s; and Richman et al (1995) Cancer Res. 55(23 Supp): 5916s-5920s); antibodies that bind to colon carcinoma cells such as C242 (Litton et al (1996) Eur J. Immunol. 26(1):1-9); anti-CD38 antibodies, e.g. AT 13/5 (Ellis et al (1995) J. Immunol. 155(2):925-937); anti-CD33 antibodies such as Hu M195 (Jurcic et al (1995) Cancer Res 55(23 Suppl):5908s-5910s and CMA-676 or CDP771; anti-CD22 antibodies such as LL2 or LymphoCide (Juweid et al (1995) Cancer Res 55(23 Suppl):5899s-5907s); anti-EpCAM antibodies such as 17-1A (PANOREX®); anti-GpIIb/IIIa antibodies such as abciximab or c7E3 Fab (REOPRO®); anti-RSV antibodies such as MEDI-493 (SYNAGIS®); anti-CMV antibodies such as PROTOVIR®; anti-HIV antibodies such as PRO542; anti-hepatitis antibodies such as the anti-Hep B antibody OSTAVIR®; anti-CA 125 antibody OvaRex; anti-idiotypic GD3 epitope antibody BEC2; anti-alpha v beta3 antibody VITAXIN®; anti-human renal cell carcinoma antibody such as ch-G250; ING-1; anti-human 17-1A antibody (3622W94); anti-human colorectal tumor antibody (A33); anti-human melanoma antibody R24 directed against GD3 ganglioside; anti-human squamous-cell carcinoma (SF-25); and anti-human leukocyte antigen (HLA) antibodies such as Smart ID10 and the anti-HLA DR antibody Oncolym (Lym-1).

"Antibody fragments" comprise a portion of a full length antibody, generally the antigen binding or variable region thereof. Examples of antibody fragments include Fab, Fab', F(ab')$_2$, and Fv fragments; diabodies; linear antibodies; fragments produced by a Fab expression library, anti-idiotypic (anti-Id) antibodies, CDR (complementary determining region), ECD (extracellular domain), and epitope-binding fragments of any of the above which immunospecifically bind to cancer cell antigens, viral antigens or microbial antigens, single-chain antibody molecules; and multispecific antibodies formed from antibody fragments.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')$_2$ antibody fragments originally were produced as pairs of Fab' fragments which have hinge cysteines between them. Other chemical couplings of antibody fragments are also known.

"Monoclonal antibody" refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al (1975) Nature 256:495, or may be made by recombinant DNA methods (see, U.S. Pat. No. 4,816,567). The "monoclonal antibodies" may also be isolated from phage antibody libraries using the techniques described in Clackson et al (1991) Nature, 352:624-628; Marks et al (1991) J. Mol. Biol., 222:581-597; for example.

"Cysteine-engineered antibodies" are antibodies engineered from wild-type or parent antibodies by the introduction of one or more free cysteine amino acids. A "free cysteine amino acid" is a cysteine amino acid residue which has been engineered into a parent antibody, has a thiol functional group (—SH), and is not paired as, or otherwise part of, an intramolecular or intermolecular disulfide bridge. The free cysteine amino acid may be in the heavy chain, light chain or Fc region of an antibody. An engineered cysteine residue ("free cysteine thiol") is reactive with thiol-reactive labelling reagents. Cysteine-engineered antibodies include FAB antibody fragments (thioFab) and expressed, full-length, IgG monoclonal (thioMab) antibodies (US 2007/0092940; WO 2008/141044, the contents of which are incorporated by reference). ThioFab and ThioMab antibodies have been conjugated through linkers at the newly introduced cysteine thiols with thiol-reactive linker reagents and drug-linker reagents to prepare antibody-drug conjugates.

"PEG" refers to a fragment of poly(ethylene glycol), a polymer of ethylene oxide, and includes 2 or more ethyleneoxy units (—$CH_2CH_2O$—).

Synthesis of Labelling Reagents

The invention includes a modular platform for rapid preparation of various water-soluble prosthetic groups capable to efficiently introduce $^{18}$F into proteins (Gill et al (2009) Jour. Med. Chem. 52(19):5816-5825). The utility of this platform is demonstrated by the thiol-specific prosthetic group and labelling reagent, [$^{18}$F] FPEGMA 5, which was rapidly produced in a two-step, one-pot synthesis (FIG. 1). Additionally, to promote the water solubility and resultant conjugation efficiency of [$^{18}$F]FPEGMA with protein in aqueous conditions, polyethylene glycol (PEG) based "building blocks" were used. [$^{18}$F]FPEGMA 5 was evaluated as a prosthetic group with 4D5ThioFab and the resulting conjugate ($^{18}$F-4D5ThioFab) was validated in vivo as an imaging agent of the HER2 expression level in a human tumor xenograft murine model modulated by an Hsp90 inhibitor (Smith-Jones et al (2006) J Nucl Med 47:793-6; Smith-Jones et al (2004) Nat Biotechnol 22:701-6).

The utility of exemplary embodiment [$^{18}$F]FPEGMA 5 demonstrates a variety of $^{18}$F-labeled prosthetic groups and labelling reagents which may be contemplated (FIG. 3), including the thiol-specific bromoacetamide compound [$^{18}$F] FPEGBA, the amino-specific N-hydroxysuccinimide (NHS) compound [$^{18}$F]FPEGNHS, the azide-specific compound [$^{18}$F]FPEG-propargyl, and the alkyne-specific compound [$^{18}$F]FPEGN$_3$. Other thiol-specific functionality may be utilized in $^{18}$F-labeled prosthetic groups and labelling reagents such as vinylsulfones as Michael acceptors, chloro- and iodoacetamides as additional sulfur alkylating reagents. Amino specific functional groups for labelling the lysine and other amino groups of proteins include various activated carboxylic acid esters such as tetrafluorophenyl ester, pentafluorophenyl ester, N-hydroxysuccinimide, and sulfohydroxysuccinimide A useful synthetic procedure is the Copper(I)-catalyzed Azide-Alkyne Cycloaddition (CuAAC) to prepare labelling reagents from azide and alkyne intermediates by 1,3-dipolar cycloaddition, sometimes referred to as "Click chemistry". The rapid reaction rates and orthogonality of the CuAAC reaction to most functional groups, including those found on biomolecules such as proteins, promotes the stability and high yield forming the 1,2,3-triazolyl group of the product. Thus, the CuAAC provides a robust method of coupling heterobifunctional precursors containing azide and alkyne functional groups.

Figure 4:
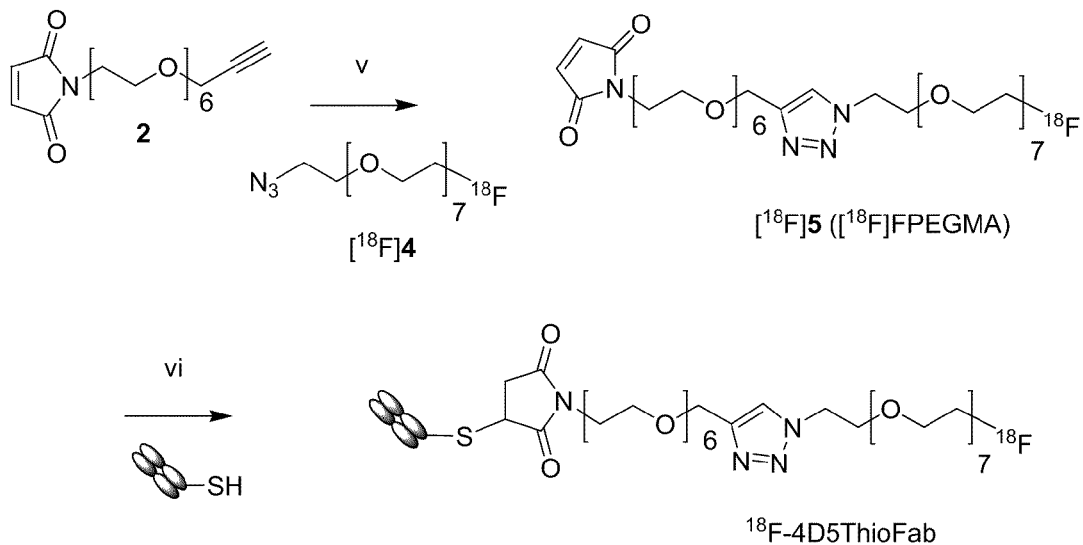
FIG. 4 shows synthesis of [$^{18}$F]FPEGMA 5 and radiolabeling of a ThioFab to give [$^{18}$F]FPEGMA-Thio4D5Fab 6. Reagents: v. CuSO$_4$.H$_2$O, BPDS, sodium ascorbate; vi. phosphate buffer pH 8

Click chemistry provides an opportunity to design labelling reagents to conjugate to proteins as PET imaging tracers, which display extremely high affinities for their biological targets. Click chemistry is a modular approach to chemical synthesis, exemplified in FIGS. 1, 2, and 4. Click chemistry techniques are described, for example, in the following references, which are incorporated herein by reference in their entirety: Kolb et al (2001) Angew. Chem. Int. Ed. 40:2004-2021; Kolb et al (2003) Drug Discovery Today 8:1128-1137; Rostovtsev et al (2002) Angew. Chem. Int. Ed. 41:2596-2599; Tornoe et al (2002) Jour. of Org. Chem. 67:3057-3064; Wang et al (2003) Jour. of the Am. Chem. Soc. 125:3192-3193; Lee et al (2003) Jour. of the Am. Chem. Soc. 125:9588-9589; Lewis et al (2002) Angew. Chem., Int. Ed. 41:1053-1057; Manetsch et al (2004) Jour. of the Am. Chem. Soc. 126: 12809-12818; Mocharla et al (2005) Angew. Chem. Int. Ed. 44:116-120; Whiting et al (2006) Angew. Chem. 118:1463-1467; Whiting et al (2006) Angew. Chem. Int. Ed. Engl. 45:1435-1439.

An example is the maleimide-bearing prosthetic group, [$^{18}$F]FPEGMA 5, which was rapidly produced in a two-step, one-pot synthesis (FIG. 1) with the copper catalyst Cu(MeCN)$_4$PF$_6$ (Example 5). A variety of other copper catalysts can be employed to form the triazole, including CuSO$_4$, CuI, CuBr, CuOTf (U.S. Pat. No. 7,375,234). The copper catalyst may be a hydrate or a solvated form. The copper reagent used may be a Cu$^0$ species such as copper wire, a Cu$^I$ salt, or a Cu$^{II}$ salt in the presence of a reducing agent such as sodium ascorbate. A bifunctional, azide-tosylate intermediate N$_3$-PEG-OTs, where PEG is a polyethyleneoxy unit of 2 to 12 ethyleneoxy groups (—CH$_2$CH$_2$O—), such as 23-azido-3,6,9,12,15,18,21-heptaoxatricos-1-yl p-toluenesulfonate 3 (Example 3) is fluorinated with $^{18}$F anion to generate the radiochemical intermediate N$_3$-PEG-$^{18}$F, exemplified by 23-azido-1-fluoro-3,6,9,12,15,18,21-heptaoxatricosane 4 (Example 4). Additionally, to promote the water solubility and resultant conjugation efficiency of [$^{18}$F]FPEGMA 5 with protein in aqueous conditions, polyethylene glycol (PEG) based "building blocks" were used. [$^{18}$F]FPEGMA 5 was evaluated as a prosthetic group with 4D5ThioFab and the resulting conjugate ($^{18}$F-4D5ThioFab 6) was validated in vivo as an imaging agent of the HER2 expression level in a human tumor xenograft murine model modulated by an Hsp90 inhibitor (Smith-Jones et al (2006) J Nucl Med 47:793-6; Smith-Jones et al (2004) Nat Biotechnol 22:701-6).

Considerations for the synthesis of [$^{18}$F]FPEGMA include the use of water-soluble building blocks with PEG chains, the implementation of microwave-accelerated heating, the coupling of reactants via the CuAAC system, and the optimization of the site-specific reaction of [$^{18}$F]FPEGMA 5 to proteins such as 4D5ThioFab with subsequent biological validation. Hydrophilic prosthetic groups may provide superior conjugation kinetics and efficiency with 4D5ThioFab and other hydrophilic proteins. Therefore, building blocks with PEG chains were investigated since they improve water-solubility without compromising solubility in organic solvents required for the nucleophilic incorporation of $^{18}$F. Prosthetic groups of the invention are more water-soluble than compounds derived from the [$^{18}$F]FBALD platform. For example, the measured log P of [$^{18}$F] 5 (−2.41±0.09) is three units from the value reported for [$^{18}$F]FBOM and over five units from [$^{18}$F]FBAM (Wuest et al (2009) Amino Acids 36:283-295). The advantage of water-soluble prosthetic groups in conjugating to 4D5ThioFab, and perhaps hydrophilic proteins in general, was validated by the observation that [$^{18}$F] 5 provided a superior conjugation efficiency compared to [$^{18}$F]FBAM under comparable conditions.

Microwave heating improved the yield of [$^{18}$F] 4 and reduced the total synthesis time of [$^{18}$F] 5 compared to conventional heating conditions. A significant acceleration of solvent heating was observed during the $^{18}$F-fluorination of 3, the azeotropic removal of water from the TBAHCO$_3$ or K222/K$_2$CO$_3$ eluent, and the evaporation of acetonitrile after alumina treatment of [$^{18}$F] 4 for methods A and B. Such advantages of microwave heating for general radiochemical use may be general. However, an important caveat is that K222/K$_2$CO$_3$ degradation was observed during the azeotropic removal of water when high microwave power (above 50 W) or temperature (above 100° C.) was used. Therefore, gentle microwave heating conditions are required to azeotropically remove water from the K222/K$_2$CO$_3$ eluent which provides a comparable evaporation time and comparable to superior $^{18}$F-fluorination yields compared to conventional heating conditions.

The CuAAC method used to couple azide and alkyne-bearing precursor reagents and produce labelling reagent [$^{18}$F] 5 was selected based on the observed reaction rate, conversion efficiency, and purity (Example 5). The low purity of [$^{18}$F] 5 observed with method A may be attributed to the instability of maleimide-based compounds in aqueous conditions over the 20 minute reaction time. Two bidentate ligands, BPDS and TBTA, which have been established as catalysts for improving the CuAAC reaction rate and the orthogonality with protein conjugations were used (Lewis et al (2004) J Am Chem Soc 126:9152-3; Rodionov et al (2007) J Am Chem Soc 129:12705-12; Rodionov et al (2007) J Am Chem Soc 129:12696-704). The dramatic improvement in purity observed for [$^{18}$F] 5 when BPDS was added to the reaction system of method A may result from the short reaction time of method B limiting the degradation of [$^{18}$F] 5 in aqueous conditions. This is reinforced by the observation that the degradation of [$^{18}$F] 5 over time was generally comparable between methods A and B. For methods A and B, TBAHCO$_3$ provided significantly less $^{18}$F-labeled degradation products than K222/K$_2$CO$_3$ which is attributed to the sensitivity of maleimide to basic reagents in aqueous conditions. The improved purity of [$^{18}$F] 5 observed when alumina treatment was included prior to CuAAC further indicates the product's sensitivity to base.

Despite the improvement in reaction time and purity observed in method B, the CuAAC reaction performed in organic solvent would promote the stability of [$^{18}$F] 5. This prompted the investigation of method C, which was performed in anhydrous acetonitrile, in which [$^{18}$F] 5 was stable and even tolerated basic reagents, such as 2,6-lutidine. However, to prevent the subsequent degradation of [$^{18}$F] 5, the CuAAC reaction was quenched with water containing 0.01% trifluoroacetic acid. In this example, method C providing a significantly higher purity compared to method A and comparable purity compared to method B. Furthermore, for more aqueous labile prosthetic groups, such as [$^{18}$F]FPEGNHS, method C provided significantly higher purity compared to methods A and B.

Comparable yields were obtained using [$^{18}$F] 4 or [$^{18}$F]FPEG$_4$N$_3$ with methods B and C. The limited water solubility observed for [$^{18}$F]FPEG$_2$N$_3$ distinguished method C. Additionally, method C does not require alumina treatment between the $^{18}$F-fluorination and CuAAC reaction steps. Therefore, method C may be well suited for general radiochemical application facilitating the development of a consistent radiochemical process for the production of a variety of $^{18}$F-labeled prosthetic groups. This may have strong implications for automation and may eliminate the need for dedicating a synthesis module to a specific prosthetic group, as is the case with [$^{18}$F]SFB.

Method B was primarily employed for the production of [$^{18}$F] 5, since the refinement of method C occurred after the optimization of [$^{18}$F] 5 and validation on 4D5ThioFab. However, method C has been confirmed to provide [$^{18}$F] 5 and $^{18}$F-4D5ThioFab with yields comparable to method B. Thus, methods B and C are both useful for the preparation of $^{18}$F-labeled proteins using [$^{18}$F] 5 and may be suitable for broader radiochemical application, using other radionuclides.

Figure 5:
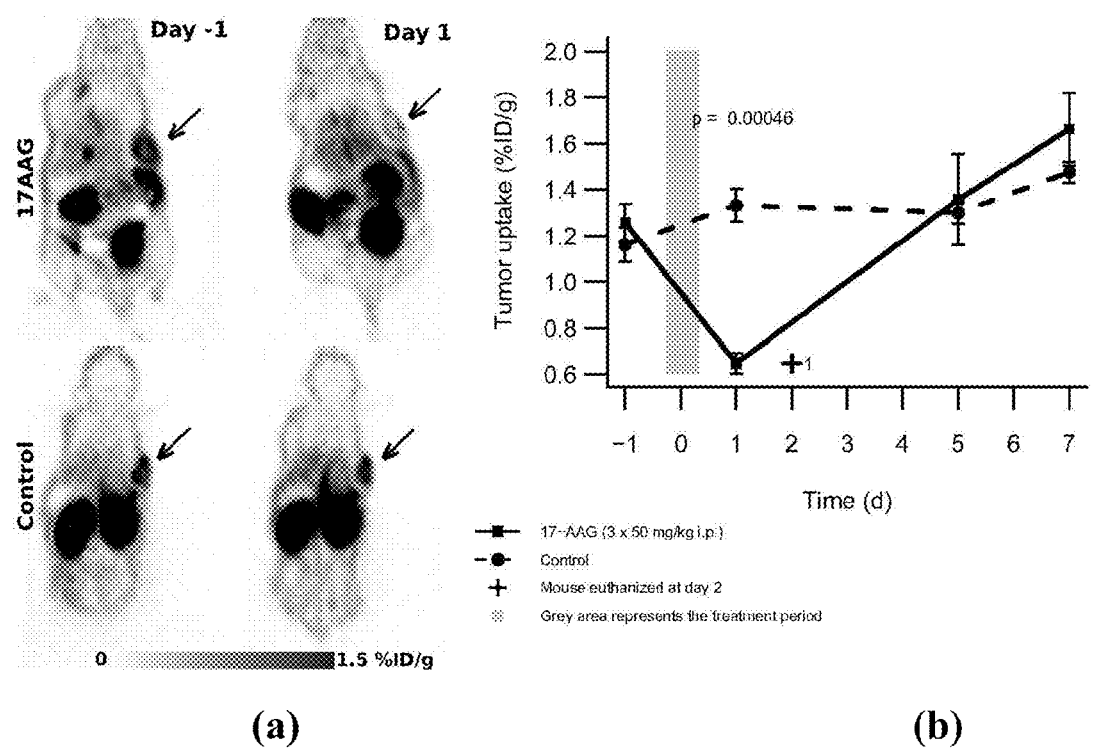
FIG. 5 shows (a) Representative microPET images (coronal slices through tumor) of animal before (day −1) and after (day 1) 17-AAG therapy (top) compared to control animal (bottom). (b) Uptake of the $^{18}$F-4D5ThioFab in the tumor tissue before and after the therapy.

The orthogonality of the CuAAC reaction facilitates the development of a variety of $^{18}$F-labeled prosthetic groups from a common reaction platform. By modifying specific properties, such as chemoselectivity and intermediate chain structure, several prosthetic groups are capable of introducing $^{18}$F into proteins and potentially peptides (FIG. 5). In addition to [$^{18}$F] 5, the amino-specific prosthetic group, [$^{18}$F]FPEGNHS 13, from a commercially available precursor, N$_3$-PEG$_4$-NHS, using method C, was conjugated to 4D5ThioFab. In addition to ensuring the stability and promoting the yield of [$^{18}$F]FPEGNHS, the labels of the invention may limit the reduction of immunoreactivity characteristic of random amino-specific modifications. For example, the steric hindrance of [$^{18}$F]FPEGNHS within the protein binding site may be reduced by using building blocks with smaller intermediate chains. Therefore, [$^{18}$F]FPEGNHS is an alternative to [$^{18}$F]SFB for performing amino-specific conjugations. Furthermore, the thiol-specific bromoacetamide analog [$^{18}$F] FPEGBA is useful for labelling proteins using method B.

A variety of $^{18}$F-labeled prosthetic groups are available, including the thiol-specific bromoacetamide compound [$^{18}$F] FPEGBA, the amino-specific N-hydroxysuccinimide (NHS) compound [$^{18}$F]FPEGNHS, the azide-specific compound [$^{18}$F]FPEG-propargyl, and the alkyne-specific compound [$^{18}$F]FPEGN$_3$.

Figure 3:
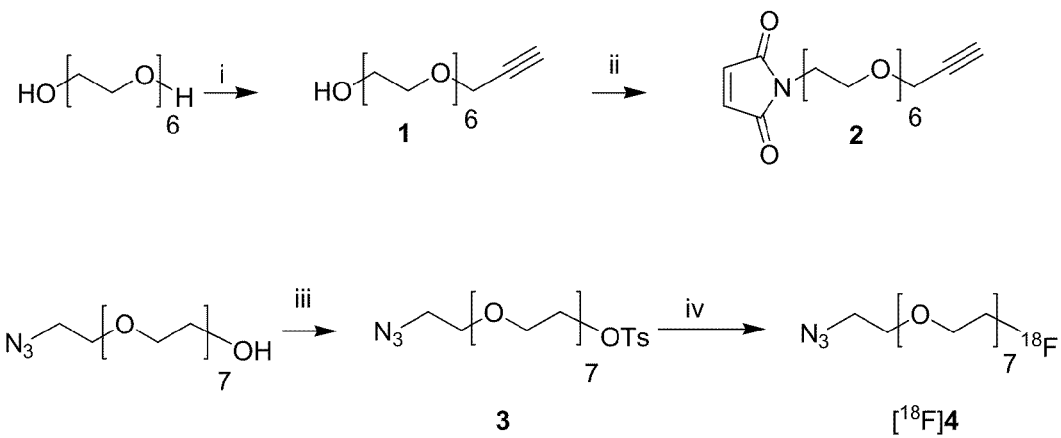
FIG. 3 shows synthesis of intermediates 2 and 4. Reagents: i. NaH, propargyl bromide; ii. maleimide, PPh$_3$, DIAD; iii. TsCl, pyridine; iv. TBAHCO$_3$, [$^{18}$F]fluoride

Detailed synthetic protocols and analytical data are presented in the Examples. FIG. 3 and the Examples outline the preparation of labelling intermediates TsO-PEG$_8$-N$_3$ 3, TsO-PEG$_4$-N$_3$ 7, and TsO-PEG$_2$-N$_3$ 8, of general utility for the production of $^{18}$F-labeled prosthetic groups, and propargyl-PEG$_6$-maleimide 2, a precursor specific for the synthesis of [$^{18}$F] 5 ([$^{18}$F]FPEGMA). Compound 3 was synthesized from commercially available heterobifunctional HO-PEG$_8$-N$_3$ and tosylchloride in pyridine with a 25% yield. Compounds 7 and 8 were synthesized in 30% and 19% yields respectively by heating equimolar amounts of NaN$_3$ and the appropriate PEG-ditosylate in DMF to 110° C. The synthesis of 2 from hexaethylene glycol required two steps; the Williamson ether synthesis was employed using equimolar amounts of NaH and propargyl bromide and provided a 54% yield of propargyl-PEG$_6$-OH 1, followed by the PPh$_3$/DIAD mediated Mitsunobu reaction with excess maleimide which provided a 25% yield of 2.

Azide reagents, N-(20-azido-3,6,9,12,15,18-hexaoxaicosyl)-2-bromoacetamide 9 and N-(20-azido-3,6,9,12,15,18-hexaoxaicosyl)-2-iodoacetamide 9a, were prepared from 20-azido-3,6,9,12,15,18-hexaoxaicosan-1-amine (NH$_2$-PEG$_7$-N$_3$). The bromoacetyl and iodoacetyl groups of 9 and 9a respectively are reactive with certain nucleophilic functional groups of proteins such as cysteine thiol groups to form azido-protein intermediates. The azido-protein intermediate can react with an $^{18}$F-PEG-alkyne reagent having the formula:

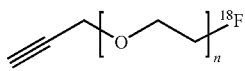

in the presence of a copper catalyst, where n is an integer from 2 to 12, to form a labelled protein.

Microwave-Accelerated Nucleophilic $^{18}$F-fluorination. Tetrabutylammonium hydrogen carbonate (TBAHCO$_3$) was selected over Kryptofix 222 and K$_2$CO$_3$ (K222/K$_2$CO$_3$) as a phase transfer catalyst for the nucleophilic fluorination of [$^{18}$F]FPEG$_2$N$_3$, [$^{18}$F]FPEG$_4$N$_3$, and [$^{18}$F]FPEG$_8$N$_3$ ([$^{18}$F] 4). Since TBAHCO$_3$ exhibited higher thermal stability relative to K222/K$_2$CO$_3$, microwave heating at high temperatures accelerated the azeotropic removal of water within 5 min. Additionally, microwave heating provided a high $^{18}$F-fluorination efficiency (89.0±1.4%, n=5) in 3 min for [$^{18}$F] 4 in acetonitrile, with comparable yields observed for [$^{18}$F]FPEG$_4$N. However, slightly reduced yields of [$^{18}$F]FPEG$_2$N$_3$ were observed due to compounds volatility at the temperatures used during the fluorination and evaporation heating steps, a problem rectified by using resealable reaction vessel caps.

Preparation of [$^{18}$F] 5. Three catalytic systems were evaluated for the conjugation of [$^{18}$F] 4 and 2 using the CuAAC reaction (Table 1). Method A (Example 5), which employs CuSO$_4$.5H$_2$O and sodium ascorbate as a source of Cu$^I$ (Glaser et al (2007) Bioconjug Chem 18:989-93), provided the desired product in 20 min with a 79.3% conversion efficiency and a 65.7% purity. The long reaction time and limited purity observed prompted the investigation of ligands capable of accelerating the CuAAC reaction. Method B adds the Cu$^I$ ligand, bathophenanthroline disulfonate (BPDS), to method A, which dramatically reduced the reaction time to 1 min, increased the conversion efficiency to 95.6%, and improved the purity to 88.7%. For methods A and B, the formation of $^{18}$F-labeled degradation products was decreased when the synthesis of [$^{18}$F] 4 was catalyzed by TBAHCO$_3$ compared to K222/K$_2$CO$_3$ and when [$^{18}$F] 4 was purified with an Alumina N Light cartridge prior to the CuAAC reaction.

Method C employs acetonitrile compatible reagents such as Cu(MeCN)$_4$PF$_6$ as a source of Cu$^I$, tris[(1-benzyl-1H-1,2,3-triazol-4-yl)methyl]amine (TBTA) as a Cu$^I$ ligand, and 2,6-lutidine as a base catalyst (Lewis et al (2004) J. Am. Chem. Soc. 126:9152-9153; Chan et al (2004) Org. Lett. 6:2853-2855). Using method C, the reaction time (less than 5 min), formation of $^{18}$F-labeled degradation products (10%), and conversion efficiency (100%) were comparable to method B. Furthermore, alumina purification of [$^{18}$F] 4 prior to the CuAAC reaction did not impact the purity of [$^{18}$F] 5 and, resultantly, was not included in method C.

After SPE treatment, method B provided [$^{18}$F] 5 with a yield of 59±4%, a radiochemical purity of 94%, and a specific activity of 5.1±1.5 Ci/μmol (determined against an HPLC standard curve of $^{19}$F-labeled 5) in 47±1 min (n=5). The identity of [$^{18}$F] 5 was confirmed by HPLC co-elution with $^{19}$F-labeled standard and by LC/MS analysis of the decayed product. The lipophilicity (log P) of [$^{18}$F]5 (-2.41±0.09) was measured at pH 7.4 consistent with published methods (Rodionov et al (2007) J Am Chem Soc 129:12705-12).

TABLE 1

Comparison of three methods for the CuAAC catalyzed conjugation of [$^{18}$F] 4 and 2, including reaction time, conversion from [$^{18}$F] 4 to [$^{18}$F] 5, and purity of crude [$^{18}$F] 5 with respect to $^{18}$F-labeled breakdown products.

| Method | Catalysts | Time (min) | % Conversion | % Purity |
|---|---|---|---|---|
| A | CuSO$_4$/ascorbate | 20 | 79.3 | 65.7 |
| B | CuSO$_4$/ascorbate/BPDS | 1 | 95.6 | 88.7 |
| C | Cu(MeCN)$_4$PF$_6$/TBTA/ 2.6-lutidine | 5 | 100 | 90.1 |

Synthesis of Labelled Proteins

Peptide labelling methods are well known. See Haugland, 2003, *Molecular Probes Handbook of Fluorescent Probes and Research Chemicals*, Molecular Probes, Inc.; Brinkley, 1992, Bioconjugate Chem. 3:2; Garman, (1997) *Non-Radioactive Labelling: A Practical Approach*, Academic Press, London; Means (1990) Bioconjugate Chem. 1:2; Glazer et al (1975) *Chemical Modification of Proteins. Laboratory Techniques in Biochemistry and Molecular Biology* (T. S. Work and E. Work, Eds.) American Elsevier Publishing Co., New York; Lundblad, R. L. and Noyes, C. M. (1984) *Chemical Reagents for Protein Modification*, Vols. I and II, CRC Press, New York; Pfleiderer, G. (1985) "Chemical Modification of Proteins", *Modern Methods in Protein Chemistry*, H. Tschesche, Ed., Walter DeGryter, Berlin and New York; and Wong (1991) *Chemistry of Protein Conjugation and Cross-linking*, CRC Press, Boca Raton, Fla.); De Leon-Rodriguez et al (2004) Chem. Eur. J. 10:1149-1155; Lewis et al (2001)

Bioconjugate Chem. 12:320-324; Li et al (2002) Bioconjugate Chem. 13:110-115; Mier et al (2005) Bioconjugate Chem. 16:240-237.

The methods described are rapid and efficient, providing $^{18}$F-radiolabeled protein ($^{18}$F-4D5ThioFab) in 82 min with a total yield of 11±3% and a specific activity of 2.0±0.2 Ci/μmol (Gill et al (2009) Jour. Med. Chem. 52(19):5816-5825). $^{18}$F-4D5ThioFab retained the biological activity of native protein and was successfully validated in vivo with microPET imaging of HER2 expression in a xenograft tumor-bearing murine model modulated by the Hsp90 inhibitor, 17-AAG. The conjugation efficiency of [$^{18}$F] 5 and 4D5ThioFab was tested as a function of protein concentration, pH, and time (Table 2). As the protein concentration and pH were increased, reduced conjugation time and increased efficiency was observed. No significant increase in the degradation of [$^{18}$F]5 or aggregation of 4D5ThioFab was observed at pH 8 relative to pH 6.5.

The proteins of the invention include cysteine engineered antibodies where one or more amino acids of any form of wild-type or parent antibody is replaced with a cysteine amino acid. The engineered cysteine amino acid is a free cysteine acid and not part of an intrachain or interchain disulfide unit. Any form of antibody may be so engineered, i.e. mutated. For example, a parent Fab antibody fragment may be engineered to form a cysteine engineered Fab, referred to herein as "ThioFab." Similarly, a parent monoclonal antibody may be engineered to form a "ThioMab." It should be noted that a single site mutation yields a single engineered cysteine residue in a ThioFab, while a single site mutation yields two engineered cysteine residues in a ThioMab, due to the dimeric nature of the IgG antibody. The cysteine engineered antibodies of the invention include monoclonal antibodies, humanized or chimeric monoclonal antibodies, antigen-binding fragments of antibodies, fusion polypeptides and analogs that preferentially bind cell-associated polypeptides. Cysteine engineered antibodies retain the antigen binding capability of their wild type, parent antibody counterparts.

The purification of $^{18}$F-ThioFab was performed on a NAP-5 desalting column and Bio-Sep S-2000 SEC-HPLC column (System D). The NAP-5 method provided significant co-elution of unconjugated [$^{18}$F] 5 with 4D5ThioFab, particularly for reactions with a low conjugation efficiency. The Bio-Sep S-2000 SEC-HPLC separated $^{18}$F-4D5ThioFab from $^{18}$F-labeled aggregates and [$^{18}$F] 5 (and $^{18}$F-labeled degradation products). The purified final product, $^{18}$F-4D5ThioFab, was analyzed by HPLC system A, system C, and TOF LC/MS. The optimized conjugation procedure provided $^{18}$F-4D5ThioFab in 26±7% yield, with greater than 90% radiochemical purity, and a specific activity of 2.0±0.2 Ci/μmol (n=5). The total synthesis time was 82±4 min from the start of synthesis and the total decay corrected yield was 11±3%.

TABLE 2

Conjugation efficiency of [$^{18}$F]5 (5 mCi, 1 nmol) to 4D5ThioFab (100 μg, 2 nmol) against protein concentration, pH, and time. The procedure for preparation of [$^{18}$F]5 was consistent with routine production; however, equal fractions of [$^{18}$F]5 (in acetonitrile after SPE treatment) were dispensed into ten reaction vials, evaporated, and 4D5ThioFab was added.

| pH | Protein conc. (mg/mL) | Yield (%) 10 min | 30 min | 60 min |
|---|---|---|---|---|
| 6.5 | 0.5 | 26 | 39 | 44 |
| 6.5 | 1.0 | 26 | 42 | 53 |
| 6.5 | 2.0 | 47 | 66 | 74 |
| 7.2 | 1.0 | 64 | 74 | 77 |
| 8.0 | 1.0 | 79 | 85 | 85 |

Figure 2:
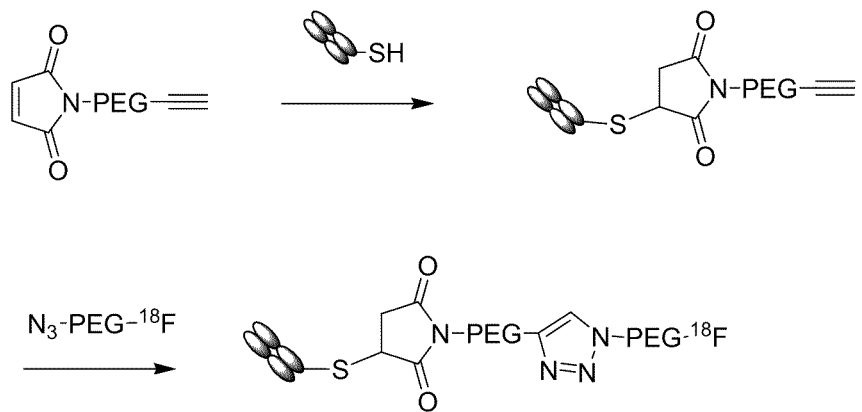
FIG. 2 shows an exemplary synthetic route for radiolabeling Fab fragments using [$^{18}$F]FPEGMA.

In addition to being precursors for the synthesis of [$^{18}$F] FPEGMA, (FIG. 1), [$^{18}$F]FPEG-propargyl and [$^{18}$F]FPEGN$_3$ can be directly conjugated to proteins via the CuAAC reaction (FIG. 2). This approach reduces the synthesis of $^{18}$F-labeled protein to two radiochemical steps and provides an alternative method for performing site-specific conjugations. Pre-conjugation of propargyl-PEG-maleimide (2) to ThioFab followed by direct CuAAC between [$^{18}$F] 4 and propargyl-PEG-ThioFab using a BPDS/Cu(MeCN)$_4$OTf system (3:1, 3 mM BPDS) with conjugation efficiencies up to 15% observed. A similar method was employed to couple [$^{18}$F] FPEG$_3$-propargyl to an azide-PEG modified cross-linked dextran iron oxide (CLIO) nanoparticle with high conjugation efficiencies resulting from the presence of numerous azide sites (Devaraj et al (2009) "$^{18}$F Labeled Nanoparticles for in Vivo PET-CT Imaging" Bioconjug Chem 10.1021/bc8004649). This technique may provide a high specific activity of $^{18}$F-labeled proteins, since [$^{18}$F] 4 is stable and multiple azide or alkyne groups may be selectively positioned on a protein without the potential for cross-reactivity. However, since Cu$^{II}$ in the presence of ascorbate tends to degrade proteins (Devaraj et al (2009) "$^{18}$F Labeled Nanoparticles for in Vivo PET-CT Imaging" Bioconjug Chem 10.1021/bc8004649), this method requires the rigorous exclusion of oxygen, the use of reducing agents, or the use of a Cu$^{I}$ stabilizing ligand such as BPDS to limit protein cleavage. Finally, [$^{18}$F]FPEG-propargyl and [$^{18}$F]FPEGN$_3$ are $^{18}$F-labelled prosthetic groups for the development of $^{18}$F-labeled peptides. In fact, the propargyl-bearing prosthetic group, [$^{18}$F] FPy5yne (Inkster et al (2008) Journal of Labelled Compounds and Radiopharmaceuticals 51:444-452), was recently evaluated with an azide-modified peptide similar to method C.

The site-specific conjugation of [$^{18}$F] 5 to 4D5ThioFab was optimized with respect to the reaction rate and reactant stability. Regarding the stability of thiol-bearing proteins, which generally decreases as pH and protein concentration increases, an increase in 4D5ThioFab dimerization and aggregation across the range of pH (6.5-8) and protein concentration (1-2 mg/mL) used to generate Table 2 was not observed. However, the formation of undesired disulfide bonds for thiol-bearing proteins likely depends on the accessibility of the thiol group. For 4D5ThioFab, the PHESELECTOR method of selecting the optimal cysteine substitution position may promote thiol stability enabling the use of higher pH and protein concentration for an extended duration. No dependence stability of [$^{18}$F] 5 during the conjugation reaction on pH was observed across the range tested in Table 2, implying the introduction of an external reactant, such as silica deposited from the HPLC column or SPE cartridge, into the conjugation reaction system capable of degrading [$^{18}$F] 5 in a concentration-dependent manner. Therefore, care should be exercised when cleaning glassware and selecting appropriate solvents, HPLC columns, and SPE cartridges. Considering the observed pH-independence of 4D5ThioFab and [$^{18}$F]5 stability, basic reaction conditions (pH 8) were selected to promote higher conjugation efficiency before the complete degradation of [$^{18}$F] 5 occurs.

The stability of [$^{18}$F]FPEGMA 5 has a significant impact on conjugation efficiency and specific activity. The conjugation efficiency of [$^{18}$F] 5 to 4D5ThioFab is dependent on the total amount of intact 5 ($^{18}$F and $^{19}$F-labeled) against the total amount of 4D5ThioFab (since each ThioFab has one accessible thiol group). The total amount of intact 5 is calculated from the total activity, specific activity, and fractional degradation of [$^{18}$F]5. For example, assuming for the moment that no degradation of [$^{18}$F]5 is present, the reported values of 5 Ci/μmol and 200 mCi for [$^{18}$F]5 provide 40 nmol of total 5. Therefore, 40 nmol of thiol groups (about 2 mg of 4D5ThioFab) is required to obtain maximum conjugation efficiency; however, since 1 mg of 4D5ThioFab is used during routine production, the expected conjugation efficiency is about 50%. The observed conjugation efficiency of 26.7% indicates that only about one-half of total 4D5ThioFab has been conjugated, which is generally confirmed by integration of the native and conjugated peaks obtained by mass spectrometry for decayed $^{18}$F-4D5ThioFab. The deviation in observed from expected conjugation efficiency is a result of the degradation of [$^{18}$F] 5, used as a limiting reagent during conjugation with ThioFab. Further improvements in conjugation efficiency and specific activity may result from the use of higher protein concentrations or a more stable maleimide building block.

Imaging of $^{18}$F Labelled Proteins

Labelled cysteine engineered antibodies of the invention are useful as imaging biomarkers and probes by the various methods and techniques of biomedical and molecular imaging such as: (i) MRI (magnetic resonance imaging); (ii) MicroCT (computerized tomography); (iii) SPECT (single photon emission computed tomography); (iv) PET (positron emission tomography) Chen et al (2004) Bioconjugate Chem. 15:41-49; (v) bioluminescence; (vi) fluorescence; and (vii) ultrasound. Immunoscintigraphy is an imaging procedure in which antibodies labeled with radioactive substances are administered to an animal or human patient and a picture is taken of sites in the body where the antibody localizes (U.S. Pat. No. 6,528,624). Imaging biomarkers may be objectively measured and evaluated as an indicator of normal biological processes, pathogenic processes, or pharmacological responses to a therapeutic intervention. Biomarkers may be of several types: Type 0 are natural history markers of a disease and correlate longitudinally with known clinical indices, e.g. MRI assessment of synovial inflammation in rheumatoid arthritis; Type I markers capture the effect of an intervention in accordance with a mechanism-of-action, even though the mechanism may not be associated with clinical outcome; Type II markers function as surrogate endpoints where the change in, or signal from, the biomarker predicts a clinical benefit to "validate" the targeted response, such as measured bone erosion in rheumatoid arthritis by CT. Imaging biomarkers thus can provide pharmacodynamic (PD) therapeutic information about: (i) expression of a target protein, (ii) binding of a therapeutic to the target protein, i.e. selectivity, and (iii) clearance and half-life pharmacokinetic data. Advantages of in vivo imaging biomarkers relative to lab-based biomarkers include: non-invasive treatment, quantifiable, whole body assessment, repetitive dosing and assessment, i.e. multiple time points, and potentially transferable effects from preclinical (small animal) to clinical (human) results. For some applications, bioimaging supplants or minimizes the number of animal experiments in preclinical studies.

Hsp90 targeted therapy and microPET imaging. Mice were distributed into two groups (n=4) according to tumor uptake and volume as determined by $^{18}$F-4D5ThioFab one day prior to 17-AAG treatment (Gill et al (2009) Jour. Med. Chem. 52(19):5816-5825). 17-AAG was administered to the treated group at day 0, while the control group animals were left untreated. PET imaging with $^{18}$F-4D5ThioFab was performed at day 1 (fourteen hours after the administration of the last 17-AAG dose), day 5, and day 7. Coronal slices through the tumor of control animals and animals treated with 17-AAG one day before and one day after therapy are shown in FIG. 5a. The average tumor uptake in control and treated groups over a one week period are shown in FIG. 5b, and the uptake in select tissues and secretory organs are listed in Table 3. PET imaging at day 1 revealed a 50% reduction (P=0.00046) in tumor uptake compared to the control group and the uptake measured at day −1 (P=0.00025) (Table 3). The renal clearance of $^{18}$F-4D5ThioFab was predominant with significant accumulation of radioactivity in the bladder and high uptake in the renal cortex (Table 3). The hepatobiliary route also contributed to tracer excretion leading to accumulation of radioactive metabolites in the large intestine and gall bladder while the retention of radioactivity in the liver was relatively low. Body weight and tumor size did not change during the seven days of imaging.

TABLE 3

Average uptake of $^{18}$F-4D5ThioFab in selected tissues of animals before the treatment (day −1) and after the treatment (day 1, 5, and 7). Kidney uptake was measured in the cortex and blood uptake was measured in the left ventricle.
Data are presented as mean ± s.d.

| 17-AAG treated | Uptake (% ID/g) | | | |
|---|---|---|---|---|
| Tissue | day −1 | day 1 | day 5 | day 7 |
| Bladder | 90.76 ± 23.40 | 63.05 ± 23.08 | 57.89 ± 9.11 | 47.11 ± 32.10 |
| Blood | 0.80 ± 0.06 | 1.31 ± 0.23 | 0.97 ± 0.04 | 0.67 ± 0.07 |
| Brain | 0.08 ± 0.01 | 0.12 ± 0.02 | 0.08 ± 0.01 | 0.06 ± 0.01 |
| Gall bladder | 3.59 ± 1.43 | 4.05 ± 1.86 | 3.58 ± 0.32 | 1.97 ± 0.71 |
| Kidney | 15.26 ± 3.02 | 20.54 ± 4.97 | 20.48 ± 6.47 | 23.92 ± 6.98 |
| Large intestine | 3.96 ± 2.05 | 4.05 ± 1.47 | 3.54 ± 1.61 | 4.19 ± 0.97 |
| Liver | 0.62 ± 0.06 | 0.97 ± 0.08 | 0.82 ± 0.10 | 0.54 ± 0.04 |
| Muscle | 0.29 ± 0.03 | 0.33 ± 0.04 | 0.25 ± 0.02 | 0.21 ± 0.04 |
| Skin | 0.44 ± 0.09 | 0.50 ± 0.05 | 0.48 ± 0.02 | 0.37 ± 0.04 |
| Tumor | 1.31 ± 0.13 | 0.65 ± 0.09 | 1.36 ± 0.34 | 1.66 ± 0.27 |

The high specific activity observed for $^{18}$F-4D5ThioFab from [$^{18}$F] 5 enabled a reduction in total injected dose of 4D5ThioFab, which may prove important for receptor saturation and target uptake particularly for cells with low cell surface receptor expression levels. However, for the 17-AAG modulation study discussed below, tumor uptake was not dependent on the total 4D5ThioFab dose (30-120 μg/animal). The dose-independent tumor uptake of $^{18}$F-4D5ThioFab may result from high HER2 expression levels for the BT474M1 cell line, which limits the potential for receptor saturation at the applied dosage.

After optimizing the conjugation of [$^{18}$F] 5 to 4D5ThioFab, the biological activity of the resulting $^{18}$F-4D5ThioFab was validated by Scatchard analysis, where no significant change in affinity of the conjugate compared to native 4D5ThioFab was observed. Furthermore, the 4D5ThioFab designed by the PHESELECTOR method and employed as a model thiol-protein retained the affinity of the parent 4D5Fab ($K_d$=0.1 nM). Additional biological validation included a treatment response study of HER2-overexpressing tumor xenografts in a murine model modulated by the HSP90 inhibitor, 17-AAG.

HER2 is a receptor tyrosine kinase of the epidermal growth factor family of transmembrane receptors and is an important target for the development of breast cancer therapeutics. 17-AAG targets the molecular chaperone Hsp90 responsible for the correct folding, stability and function of wide range of oncoproteins including HER2. The effect of 17-AAG on HER2-positive tumors has been described (Solit et al (2002) Clin Cancer Res 8:986-93). The effect of 17-AAG on the HER2 expression level in a breast cancer xenograft (BT474) murine model with $^{68}$Ga-DOTA conjugated trastuzumab-F(ab')$_2$ ($^{68}$Ga-DCHF) was investigated (Smith-Jones et al (2006) J Nucl Med 47:793-6; Smith-Jones et al (2004) Nat Biotechnol 22:701-6). A 70% reduction in HER2 levels lasting five days was observed followed by a return to pretreatment levels after 12 days, suggesting that $^{68}$Ga-DCHF is capable of monitoring tumor response to 17-AAG treatment earlier than $^{18}$FDG PET. However, the short half-life of $^{68}$Ga (68 min) does not ideally match the relatively long plasma half-life of F(ab')$_2$ and a significant signal decrease is inherent within the required three hour period before PET acquisition. The relatively short plasma half-life of monovalent Fab fragments in combination with $^{18}$F (110 min) may provide improved imaging properties (Williams et al (2001) Cancer Biother Radiopharm 16:25-35).

The observed decrease of HER2 expression (FIG. 5) was broadly comparable to the that seen by Smith-Jones with F(ab')$_2$ based imaging agent. The lower decrease (50%) in $^{18}$F-4D5ThioFab tumor uptake one day after 17-AAG therapy (FIG. 5) compared to the decrease observed by Smith-Jones et al using $^{68}$Ga-DCHF (70%) may be attributed to several factors. Although the rapid renal excretion of $^{18}$F-4D5ThioFab provides an improved tumor to background ratio, a monovalent Fab fragment has a lower baseline tumor uptake compared to bivalent F(ab')$_2$. Assuming a similar post-treatment tumor uptake for Fab and F(ab')$_2$, resulting from the non-specific uptake and vasculature distribution of the tracer as shown in FIG. 5a (top-right), the percent difference for tracer uptake may be biased against the compound with a lower magnitude signal prior to treatment. This is reinforced by observation that the average tumor uptake 0.65±0.09% ID/g after 17-AAG treatment (day 1) was roughly comparable to the skin uptake 0.50±0.05% ID/g as shown in Table 3. Additionally, since 17-AAG has limited solubility in water, the formulation (consisting of an emulsion of egg phospholipid based liposomes prepared by sonication) may not have reproduced the reported potency. This may account for the faster rebound of HER2 expression in the experiment (100% at day 5). Although the magnitude of the signal decline after the 17-AAG treatment was slightly lower than previously observed (Smith-Jones et al (2006) J Nucl Med 47:793-6; Smith-Jones et al (2004) Nat Biotechnol 22:701-6), the image quality obtained with $^{18}$F-4D5ThioFab (FIG. 5) was superior compared to $^{68}$Ga-DCHF. The rapid renal clearance of the Fab fragment and the resultant enhancement to the tumor to background ratio overcame the reduced absolute magnitude of tumor uptake compared to the F(ab')$_2$ fragment. This facilitated the acquisition of data only two hours, or about one half-life, after tracer administration which provided more signal than the nearly three half-life period prior to imaging with $^{68}$Ga-DCHF.

Pharmaceutical Compositions

Pharmaceutical compositions or formulations of the present invention include a labelled protein of the invention, and one or more pharmaceutically acceptable carrier, glidant, diluent, or excipient.

Pharmaceutical compositions encompass both the bulk composition and individual dosage units comprised of more than one (e.g., two) pharmaceutically active agents including a labelled protein along with any pharmaceutically inactive excipients, diluents, carriers, or glidants. The bulk composition and each individual dosage unit can contain fixed amounts of the aforesaid pharmaceutically active agents. The bulk composition is material that has not yet been formed into individual dosage units. An illustrative dosage unit is an oral dosage unit such as tablets, pills, capsules, and the like. Similarly, the methods of administering a pharmaceutical composition to a patient is also intended to encompass the administration of the bulk composition and individual dosage units.

Pharmaceutical compositions also embrace isotopically-labeled compounds of the present invention which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine and iodine, such as $^2$H, $^3$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I and $^{125}$I. Certain isotopically-labeled compounds of the present invention (e.g., those labeled with $^3$H and $^{14}$C) are useful in compound and/or substrate tissue distribution assays. Tritiated ($^3$H) and carbon-14 ($^{14}$C) isotopes are useful for their ease of preparation and detectability. Further, substitution with heavier isotopes such as deuterium ($^2$H) may afford certain diagnostic advantages resulting from greater metabolic stability (e.g., increased in vivo half-life or reduced dosage requirements) and hence may be preferred in some circumstances. Positron emitting isotopes such as a $^{18}$F are useful for positron emission $^{15}$O, $^{13}$N, $^{11}$C and $^{18}$ tomography (PET) studies to examine substrate receptor occupancy. Isotopically labeled compounds of the present invention can generally be prepared by following procedures analogous to those disclosed in the Examples herein, by substituting an isotopically labeled reagent for a non-isotopically labeled reagent.

Suitable carriers, diluents, additives, and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), dimethylsulfoxide (DMSO), cremophor (e.g. CREMOPHOR EL®, BASF). and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an effective presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration. For example, a labelled protein having the desired degree of purity may optionally be mixed with pharmaceutically acceptable diluents, carriers, excipients or stabilizers (Remington's Pharmaceutical Sciences (1995) 18th edition, Mack Publ. Co., Easton, Pa.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. The pharmaceutical formulation is preferably sterile. In particular, formulations to be used for in vivo administration must be sterile. Such sterilization is readily accomplished by filtration through sterile filtration membranes. The pharmaceutical formulation ordinarily can be stored as a solid composition, a lyophilized formulation or as an aqueous solution.

The pharmaceutical formulations of the invention will be dosed and administered in a fashion, i.e., amounts, concentrations, schedules, course, vehicles and route of administration, consistent with good medical practice. Factors for consideration in this context include the particular disorder being diagnosed or treated, the particular mammal being treated, the clinical condition of the individual patient, the cause of the disorder, the site of delivery of the agent, the method of administration, the scheduling of administration, and other factors known to medical practitioners. The "pharmaceutically effective amount" of the compound to be administered will be governed by such considerations, and is the minimum amount necessary to diagnose, prevent, ameliorate, or treat the disorder.

The initial pharmaceutically effective amount of the labelled protein administered orally or parenterally per dose will be in the range of about 0.01-1000 mg/kg, namely about 0.1 to 20 mg/kg of patient body weight per day, with the typical initial range of compound used being 0.3 to 15 mg/kg/day. The dose of the labelled protein and the dose of the chemotherapeutic agent to be administered may range for each from about 1 mg to about 1000 mg per unit dosage form, or from about 10 mg to about 100 mg per unit dosage form. The doses of labelled protein and the chemotherapeutic agent may administered in a ratio of about 1:50 to about 50:1 by weight, or in a ratio of about 1:10 to about 10:1 by weight.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, CREMOPHOR EL®, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nanoparticles and nanocapsules) or in macroemulsions. Such techniques are disclosed in Remington's Pharmaceutical Sciences 18th edition, (1995) Mack Publ. Co., Easton, Pa.

The pharmaceutical formulations include those suitable for the administration routes detailed herein. The formulations may conveniently be presented in unit dosage form and may be prepared by any of the methods well known in the art of pharmacy. Techniques and formulations generally are found in Remington's Pharmaceutical Sciences $18^{th}$ Ed. (1995) Mack Publishing Co., Easton, Pa. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Pharmaceutical compositions may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may be a solution or a suspension in a non-toxic parenterally acceptable diluent or solvent, such as a solution in 1,3-butanediol or prepared from a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host and the particular mode of administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

Metabolites of Labelled Proteins

Also falling within the scope of this invention are the in vivo metabolic products of Labelled proteins described herein. Such products may result for example from the oxidation, reduction, hydrolysis, amidation, deamidation, esterification, deesterification, enzymatic cleavage, and the like, of the administered compound. Accordingly, the invention includes metabolites of labelled proteins, including compounds produced by a process comprising contacting a compound of this invention with a mammal for a period of time sufficient to yield a metabolic product thereof. The metabolite structures may be determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Articles of Manufacture

In another embodiment of the invention, an article of manufacture, or "kit", containing labelled proteins useful for diagnosis of diseases and disorders is provided. In one embodiment, the kit comprises a container comprising a labelled protein. The kit may further comprise a label or package insert, on or associated with the container. The term "package insert" is used to refer to instructions customarily included in commercial packages of diagnostic products, that contain information about the usage, dosage, administration, contraindications and/or warnings concerning the use of such diagnostic products. Suitable containers include, for example, bottles, vials, syringes, blister pack, etc. The container may be formed from a variety of materials such as glass or plastic. The container may hold a labelled protein or a formulation thereof and may have a sterile access port (for example, the container may be an intravenous solution bag or a vial having a stopper pierceable by a hypodermic injection needle). At least one active agent in the composition is a labelled protein. In one embodiment, the label or package inserts indicates that the composition comprising a labelled protein can be used to diagnose a disorder resulting from abnormal cell growth. The label or package insert may also indicate that the composition can be used to diagnose other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes. The kit may further comprise directions for the administration of the pharmaceutical formulation of the labelled protein.

EXAMPLES

The methods and reagents of Gill et al (2009) Jour. Med. Chem. 52(19):5816-5825 are expressly incorporated herein by reference.

Solvents and chemicals were purchased from Aldrich (Milwaukee, Wis.) unless stated otherwise. Heterobifunctional polyethylene glycols were purchased from Iris Biotech (Marktredwitz, Germany) and $N_3$-$PEG_8$-NHS was purchased from Quanta Biodesign (Powell, Ohio). Egg-phospholipid was purchased from Avanti Polar lipids (Alabaster, Ala.) and 17-(allylamino)-17-demethoxygeldanamycin (17-AAG) was obtained from InvivoGen (San Diego, Calif.). The following reversed-phase HPLC systems were used to analyze and purify the products. System A: Phenomenex Jupiter C18 300 Å (150×4.6 mm, 5 μm), 0.05% TFA+10-90% acetonitrile, 0-7 min, 20-90% acetonitrile, 7 min, 2 mL/min; System B: Phenomenex Luna C18 (250×10 mm, 5 μm) 0.05% TFA+ acetonitrile, 5 mL/min; System C: Phenomenex BioSep-SEC-S 2000 (300×4.60 mm, 5 μm) 50 mM PBS 0.5 ml/min; System D: Phenomenex BioSep-SEC-S 2000 (300×7.80 mm, 5 μm) 20 mM PBS pH7.2 1.0 ml/min; System E: Altima C-18 (100×22.0 mm, 5 μm) 0.05% TFA+10-60% acetonitrile, 0-30 min, 24 mL/min. Both analytical and semi-preparative HPLC systems used in radiochemistry were equipped with UV absorbance and radioactivity detector (PMT). [$^{18}$F]Fluoride was purchased from PETNET Solutions (PaloAlto, Calif.). Oasis HLB Plus cartridges were obtained from Waters (Milford, Mass.). $^{18}$F Trap & Release Columns (8 mg) were purchased from ORTG, Inc. (Oakdale, Tenn.). Mass spectrometry analysis of low molecular weight products was performed on PE Sciex API 150EX LCMS system equipped with Onyx Monolithic $C_{18}$ column. LC/MS analysis of proteins was performed on a TSQ Quantum Triple quadrupole mass spectrometer with extended mass range (Thermo Electron). Samples were chromatographed on a PRLP-S, 1000 Å, microbore column (50 mm×2.1 mm, Polymer Laboratories) heated to 75° C. A linear gradient from 30-40% B (solvent A, 0.05% TFA in water; solvent B, 0.04% TFA in acetonitrile) was used and the eluant was directly ionized using the electrospray source. Data were collected by the Xcalibur data system and deconvolution was performed using ProMass (Novatia). NMR spectra were recorded on Bruker Avance II 500 or Bruker Avance II 400 spectrometer at 298 K. The $^1$H and $^{13}$C chemical shifts are reported relative to TMS and the $^{19}$F chemical shifts are reported using TFA as an external reference standardized to −78.5 ppm. Model 521 microwave heater, Resonance Instruments (Skokie, Ill.), was used for radiochemical reactions. TBTA (Tris-[(1-benzyl-1H-1,2,3-triazol-4-yl)methyl]amine, also known as tris-(benzyltriazolylmethyl)amine), a stabilizing ligand for Cu(I), was synthesized according the previously published procedure in 40% yield (Lewis, et al (2004) J Am Chem Soc 126:9152-3). Strata SDB-L cartridges were purchased from Phenomenex (Torrance, Calif.).

Example 1

3,6,9,12,15,18-hexaoxahenicos-20-yn-1-ol 1

Sodium hydride, 60% dispersion in mineral oil, (0.86 g, 21.4 mmol) was added in portions to the solution of hexaethylene glycol (5.5 g, 19.4 mmol) in anhydrous THF (40 mL) at 0° C. (FIG. 3). The reaction mixture was stirred at 0° C. for 15 minutes then propargyl bromide, 80% in toluene, (2.4 mL, 21.4 mmol) was added dropwise. The mixture was allowed to warm to room temperature and stirred for 3 hours. The formed sodium bromide was removed by filtration and the solvent was evaporated. The crude product was purified on SiO$_2$ column using methanol/dichloromethane gradient 0-100% to yield 3.4 g (54%) of 1 as a colorless oil. $^1$H NMR (500 MHz, CDCl$_3$): δ 2.45 (t, J=2.4 Hz, 1H), 2.74 (bs, 1H), 3.61-3.71 (m, 24H), 4.21 (d, J=2.4 Hz, 2H); $^{13}$C NMR (100.6 MHz, CDCl$_3$): δ 58.4, 61.7, 69.1, 70.3-70.6, 72.5, 74.5, 79.7; MS ESI (m/z): [M+H]$^+$ calcd. for C$_{15}$H$_{29}$O$_7$, 321.38; found 321.4.

Example 2

1-(3,6,9,12,15,18-hexaoxahenicos-20-yn-1-yl)-2,5-pyrroledione

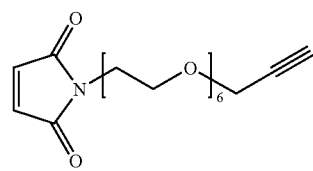

Diisopropyl azodicarboxylate (730 μL, 3.43 mmol) was added dropwise into the ice cooled solution of 3,6,9,12,15,18-hexaoxahenicos-20-yn-1-ol 1 (1000 mg, 3.12 mmol), triphenylphosphine (900 mg, 3.43 mmol) and maleimide (456 mg, 4.70 mmol) in anhydrous THF (20 mL) under nitrogen atmosphere (FIG. 3). The resulting brown solution was allowed to war to room temperature and stirred for 1 hour at room temperature. The solvent was evaporated at the reduced pressure and the crude product was purified on a SiO$_2$ column using hexanes/ethylacetate gradient 0-100% to yield 650 mg of yellow oil which was subsequently purified on semi-preparative HPLC (System E) to provide 2 free of triphenylphosphine oxide as colorless oil 310 mg (25%). $^1$H NMR (400 MHz, CDCl$_3$): δ 2.43 (t, J=2.36 Hz, 1H), 3.60-3.72 (m, 24H), 4.20 (d, J=2.37 Hz, 2H), 6.70 (s, 2H); $^{13}$C NMR (100.6 MHz, CDCl$_3$): δ 37.2, 58.4, 67.8, 69.1, 70.1, 70.4-70.6, 74.5, 79.7, 134.1, 170.6; MS ESI (m/z): [M+H]$^+$, calcd. for C$_{19}$H$_{30}$NO$_8$, 400.19; found 400.0

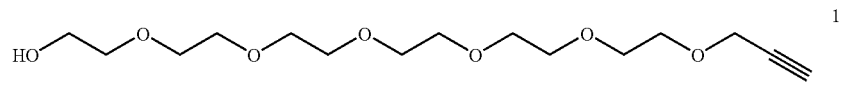 [SMILES: C#CCOCCOCCOCCOCCOCCOCCO]

Example 3

23-azido-3,6,9,12,15,18,21-heptaoxatricos-1-yl p-toluenesulfonate 3

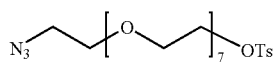

A solution of 23-azido-3,6,9,12,15,18,21-heptaoxatricosan-1-ol (800 mg, 2.02 mmol) in pyridine (4 mL) was added dropwise to the solution of toluenesulfonyl chloride (771 mg, 4.04 mmol) and 4-dimethylaminopyridine (100 mg) in pyridine (10 mL) at room temperature. The mixture was stirred for 24 hours at room temperature. The solvent was evaporated and the crude product was purified on SiO$_2$ column using hexanes/ethylacetate gradient 0-100% followed by ethylacetate/methanol gradient 0-100%, then purified on semipreparative HPLC (System E) to yield 280 mg (25%) of 3 as a colorless oil. $^1$H NMR (400 MHz, CDCl$_3$): δ 2.45 (s, 3H), 3.38 (t, J=5.02 Hz, 2H), 3.58-3.70 (m, 28H), 4.16 (t, J=5.00 Hz, 2H), 7.34 (d, J=8.4 Hz, 2H), 7.80 (d, J=8.4 Hz, 2H); $^{13}$C NMR (100.6 MHz, CDCl$_3$): δ 21.6, 50.7, 68.7, 69.2, 70.0, 70.5-70.8, 128.0, 129.7, 133.1, 144.7; MS ESI (m/z): [M+H]$^+$ calcd. for $C_{23}H_{39}N_3O_{10}S$ 549.24; found 549.9.

Example 4

23-azido-1-fluoro-3,6,9,12,15,18,21-heptaoxatricosane 4

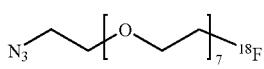

4

23-Azido-3,6,9,12,15,18,21-heptaoxatricosan-1-ol (500 mg, 1.26 mmol) was dissolved in DCM (2 mL) and cooled to −10° C. DAST (482 µL, 3.78 mmol) was added in portions to the cooled solution and the resulting mixture was stirred at −10° C. for 30 minutes then allowed to warm to room temperature and stirred for additional 20 hours. The excess of DAST was quenched with methanol (5 mL) and the solvents were subsequently evaporated at the reduced pressure. The oily residue was dissolved in the water (3 mL) and the pH was adjusted to 5 using NaHCO$_3$. The crude product was purified on semipreparative HPLC (System E) to yield 122 mg (24%) of 4 as a yellowish oil. $^1$H NMR (500 MHz, CDCl$_3$): δ 3.39 (t, J=5.0 Hz, 2H), 3.65-3.68 (m, 26H), 3.75 (dt, J=4.2 Hz, 29.6 Hz, 2H), 4.56 (dt, J=4.0 Hz, 47.5 Hz, 2H); $^{13}$C NMR (125.7 MHz, CDCl$_3$): δ 50.8, 70.1, 70.4, 70.5, 70.7-70.8, 70.9, 83.2 (d, J=169 Hz); $^{19}$F NMR (470.6 MHz, CDCl$_3$): δ-225.9; MS ESI (m/z): [M+H]$^+$ calcd. for $C_{16}H_{33}FO_7N_3$, 398.2; found 398.0.

Alternatively, and to prepare [$^{18}$F] 4, [$^{18}$F]fluoride was eluted from T&R cartridge into a 4 mL v-vial using 10 µL 1.3M TBAHCO$_3$ in 0.6 mL of acetonitrile/water 1:1 (v/v). Water was azeotropically removed by microwave heating at 60 W, 120° C. under a stream of argon (600 ccm) followed by the addition of anhydrous acetonitrile (4×0.7 mL). 23-Azido-3,6,9,12,15,18,21-heptaoxatricos-1-yl p-toluenesulfonate 3 (2 mg, 3.6 µmol) dissolved in acetonitrile (0.6 mL) was added and the mixture was microwave heated in a septum-sealed vessel at 40 W, 120° C. for 3 min to give [$^{18}$F] 23-azido-1-fluoro-3,6,9,12,15,18,21-heptaoxatricosane 4.

Example 5

1-(1-fluoro-3,6,9,12,15,18,21-heptaoxatricos-23-yl)-4-(1-(2,5-pyrrolidone-1-yl)-3,6,9,12,15,18-hexaoxanonadeca-19-yl)-1,2,3-triazole (5, FPEGMA)

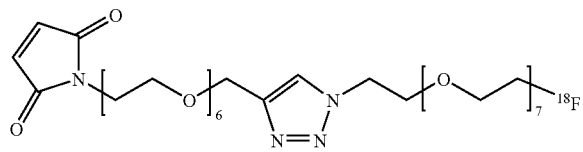

Cu(MeCN)$_4$PF$_6$ (7.5 mg, 0.02 mmol) dissolved in acetonitrile (0.1 mL) was added at room temperature to a solution of 1-(3,6,9,12,15,18-hexaoxahenicos-20-yn-1-yl)-2,5-pyrroledione 2 (8.0 mg, 0.02 mmol), 23-azido-1-fluoro-3,6,9,12,15,18,21-heptaoxatricosane 4 (8.0 mg, 0.02 mmol), 2,6-lutidine (2.5 µL, 0.02 mmol) and TBTA (2.0 mg, 0 004 mmol) in acetonitrile (0.2 mL). The resulting mixture was stirred for 22 hours at room temperature then diluted with water to 4 mL, and the formed precipitate was removed by filtration. The filtrate containing the product was purified on the semipreparative HPLC (System E) to provide 7.5 mg (47%) of 5 (FPEGMA) as a colorless oil. $^1$H NMR (500 MHz, CDCl$_3$): δ 3.58-3.80 (m. 50H), 3.87 (t, J=4.5 Hz, 2H), 4.53 (t, J=5.0 Hz, 2H), 4.55 (dt, J=47.3, 4.2 Hz, 2H), 4.68 (s, 2H), 6.70 (s, 2H), 7.73 (s, 1H); $^{13}$C NMR (125.7 MHz, CDCl$_3$): δ 37.2, 50.3, 64.7, 67.9, 69.5, 69.7, 70.2, 70.6-70.7, 70.9, 83.2 (d, J=169 Hz), 123.8, 134.2, 145.0, 170.7; $^{19}$F NMR (470.6 MHz, CDCl$_3$): δ −225.8; MS ESI (m/z): [M+H]$^+$ calcd. for $C_{35}H_{62}FO_{15}N_7$, 797.4; found 797.4; HPLC (System A) retention time 2.91 min.

Method A.

Alternatively, to prepare [$^{18}$F] 5, [$^{18}$F] 23-azido-1-fluoro-3,6,9,12,15,18,21-heptaoxatricosane 4 was passed across a Sep-Pak Alumina N light cartridge, rinsed with acetonitrile (0.5 mL), evaporated to near dryness, and cooled to 30° C. Compound 2 (4 mg 10.0 µmol) dissolved in acetonitrile (0.2 mL) was added to [$^{18}$F] 4, followed by a solution of freshly prepared sodium ascorbate (7.5 mg, 40 µmol) in 0.1 mL Tris buffer pH 8 and CuSO$_4$.5H$_2$O (2.2 mg, 8 µmol) in Tris buffer pH 8 (0.2 mL) as in FIG. 4. The resulting brown-orange solution was stirred at room temperature for 20 min followed by the addition of H$_2$O with 0.1% TFA (1 mL) and delivered to the HPLC loop for purification.

Method B.

Alternatively, to prepare [$^{18}$F] 5, [$^{18}$F] 23-azido-1-fluoro-3,6,9,12,15,18,21-heptaoxatricosane 4 was passed across a Sep-Pak Alumina N light cartridge, rinsed with acetonitrile (0.5 mL), evaporated to near dryness, and cooled to 30° C. Compound 2 (4 mg 10.0 µmol) dissolved in acetonitrile (0.2 mL) was added to [$^{18}$F] 4, followed by freshly prepared sodium ascorbate (7.5 mg, 40 µmol) in 0.1 mL Tris buffer pH 8 and a mixture of CuSO$_4$.5H$_2$O (2.2 mg, 8 µmol) and bathophenanthroline disulfonate (BPDS) (4.4 mg, 8 µmol) in Tris buffer pH 8 (0.2 mL). The resulting brown-orange solution was stirred at room temperature for 1 min followed by the addition of H$_2$O with 0.1% TFA (1 mL) and delivery to the HPLC loop for purification.

Method C.

Alternatively, to prepare [$^{18}$F] 5, [$^{18}$F] 23-azido-1-fluoro-3,6,9,12,15,18,21-heptaoxatricosane 4 was evaporated to near dryness (no alumina treatment required), after which compound 2 (4 mg, 10.0 µmol) dissolved in acetonitrile (0.1 mL) was added. Next, a freshly prepared mixture of Cu(MeCN)$_4$PF$_6$ (3 mg, 8 µmol), TBTA (4.3 mg, 8 µmol), and 25 µL 2,6-lutidine in acetonitrile (0.2 mL) was added. The resulting light yellow solution was stirred for 10 min at room temperature, concentrated to 100 µL, diluted with H$_2$O with 0.1% TFA (1 mL), and delivered to the HPLC loop for purification.

The crude product [$^{18}$F] 5 was purified by semi-preparative HPLC (system B) with a retention time of 15-18 min. The collected fraction was promptly diluted to 20 mL with H$_2$O, loaded on a Phenomenex Strata-X 60 mg SPE cartridge, the product trapped on the cartridge was rinsed with H$_2$O (10 mL), flushed with air, eluted with acetonitrile (0.5 mL) into a 1 mL v-vial, and evaporated at 30° C. to near dryness with 600 ccm argon. MS ESI (m/z): [M+H]$^+$ calcd. for $C_{35}H_{62}FO_{15}N_7$ 797.4; found 797.4; HPLC (System A) retention time 2.98 min.

To limit the degradation of [$^{18}$F] 5 in aqueous conditions, optimizations of the radiochemical process were designed to minimize the synthesis time between the CuAAC reaction and recovery from the Solid Phase Extraction (SPE). An improved yield of [$^{18}$F]5 was observed when the CuAAC reaction system was promptly quenched with 0.1% TFA water, the HPLC was conducted at a high flow rate (8 mL/min), and [$^{18}$F] 5 was promptly loaded on and eluted from the SPE cartridge. Formation of $^{18}$F-labeled degradation products from [$^{18}$F]5 increased with SPE resin bed volume and when the product remained on the resin bed for an extended period. Thus, [$^{18}$F]5 was rapidly eluted from a small volume Phenomenex Strata-X 60 mg cartridge, which provided good recovery and acceptable impurity levels.

Example 6

[$^{18}$F]FPEGMA-Thio4D5Fab 6

4D5-ThioFab was prepared similar to a previously described procedure (Junutula, J. R. et al (2008) J Immunol Methods 332:41-52; US 2007/0092940). A cysteine substitution was introduced into a Trastuzumab (4D5, Herceptin) antibody construct at position Val$^{110}$ in the light chain by site-directed mutagenesis. The expressed and purified 4D5-ThioMab was diluted to 1 mg/mL in 25 mM Tris, pH 8.0, and enzymatically digested at 37° C. for 1 hr using Lys-C (Wako) at a 1:1000 (wt:wt) ratio of enzyme to antibody. The digestion was stopped with 5 µM of the protease inhibitor tosyl-L-lysine chloromethyl ketone (TLCK) and purified by cation ion exchange chromatography on a 5 mL Hi-Trap SP FF column (GE Healthcare) using a 50 mM sodium acetate buffer and a 0-300 mM NaCl 10 CV gradient. The isolated ThioFab was then prepared for conjugation by a reduction and oxidation procedure to remove disulfide adducts bound to Cys$^{110}$. First, the protein was reduced for 24 hrs by the addition of 2 mM tris(2-carboxyethyl)phosphine (TECP) (Pierce) in a buffer containing 25 mM MES, pH 5.8, 300 mL NaCl, and 5 mM EDTA. After reduction, the protein was oxidized by the addition of 5 mM dehydroascobric acid (Sigma) and purified by gel filtration using an 5200 column (GE Healthcare) and a buffer containing 25 mM MES, pH 5.8, 300 mM NaCl, and 5 mM EDTA. The isolated protein was analyzed by SDS-PAGE and mass spectrometry to ensure that the protein was properly reduced and oxidized.

4D5ThioFab (1.0 mg, 12.6 nmol) in 100 mM sodium phosphate pH 8 (2 mg/mL) was added to [$^{18}$F] 5, and shaken on a test tube rocker for 10 min. The crude product was purified by semi-preparative SEC-HPLC column (System D, 10-12 min retention time), and, if necessary, concentrated for injection with an Amicon 10 kDa membrane. HPLC (System A) retention time 3.3 min; SEC HPLC (System C) retention volume 3.0 mL to give 6.

Example 7

5-azido-3-oxa-pentyl p-toluenesulfonate 7

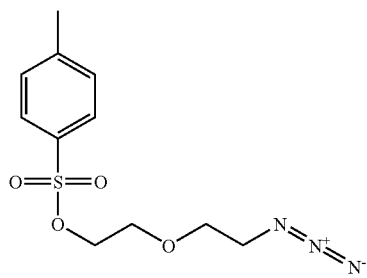

Sodium azide (0.47 g, 7.24 mmol) added to a solution of diethyleneglycol ditosylate (3 g, 7.24 mmol) in DMF (30 mL) and the resulting mixture was heated to 110° C. for 5 hours. The reaction mixture was poured into chilled water (125 mL) and the product was extracted with ethyl acetate (3×100 mL), the collected organic extracts were washed with water (3×100 mL), brine and dried over MgSO$_4$. The crude product was purified on SiO$_2$ and DCM/MeOH 0-100% gradient as eluant to yield 0.34 g (16%) of 7 as a colorless oil. $^1$H NMR (400 MHz, CDCl$_3$): δ 2.45 (s, 3H), 3.16 (t, J=4.8 Hz, 2H), 3.60 (t, J=4.8 Hz, 2H), 3.70 (t, J=4.8 Hz, 2H), 4.17 (t, J=4.8 Hz, 2H), 7.35 (d, J=8 Hz, 2H), 7.81 (d, J=8 Hz, 2H); $^{13}$C NMR (100.6 MHz, CDCl$_3$): δ 21.6, 50.6, 68.7, 69.1, 70.2, 128.0, 129.9, 133.0, 144.9; MS ESI (m/z): [M+H]$^+$ calcd. for C$_{11}$H$_{15}$N$_3$O$_4$S, 286.08; found 286.1

Example 8

11-azido-3,6,9-trioxa-undecanyl p-toluenesulfonate 8

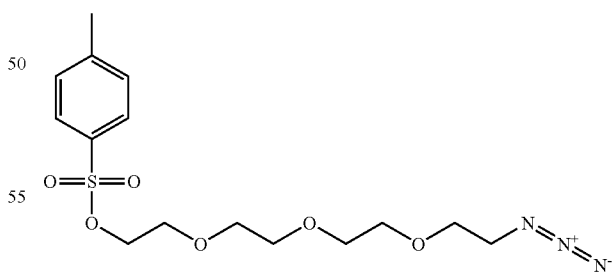

Sodium azide and tetraethylene glycol ditosylate were reacted according Example 7 p to yield 0.7 g (19%) of 8 as a colorless oil. $^1$H NMR (400 MHz, CDCl$_3$): δ 2.44 (s, 3H), 3.38 (t, J=5.2 Hz, 2H), 3.55-3.70 (m, 12H), 4.16 (t, J=5.2 Hz, 2H), 7.34 (d, J=8.4 Hz, 2H), 7.78 (d, J=8.4 Hz, 2H); $^{13}$C NMR (100.6 MHz, CDCl$_3$): δ 21.6, 50.7, 68.7, 68.8, 69.2, 70.0, 70.6-70.7, 127.9, 129.8, 133.1, 144.7 MS ESI (m/z): [M+H]$^+$ calcd. for C$_{15}$H$_{24}$O$_6$N$_3$S, 374.2; found 374.2

Example 9

N-(20-azido-3,6,9,12,15,18-hexaoxaicosyl)-2-bromoacetamide (9, $N_3$-$PEG_6$-BA)

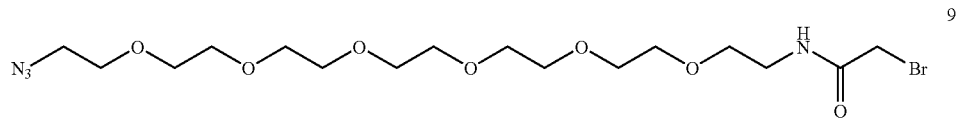 [SMILES: [N-]=[N+]=NCCOCCOCCOCCOCCOCCOCCNC(=O)CBr]

A solution of 20-azido-3,6,9,12,15,18-hexaoxaicosan-1-amine ($NH_2$-$PEG_6$-$N_3$ (0.5 g, 1.43 mmol) and triethylamine (0.2 mL, 1.43 mmol) in DCM (5 mL) was added drop wise to the cooled (0° C.) solution of bromoacetylbromide (0.190 mL, 2.15 mmol) in DCM (10 mL). The cooling bath was removed and the mixture was stirred for 90 minutes. The solution was poured into iced water (10 mL) and extracted with DCM (2×10 mL). The collected organic extracts were washed with brine (2×10 mL) and dried over $MgSO_4$. The solvent was evaporated and the crude product was purified using flash chromatography on $SiO_2$ and DCM/MeOH 0-100% gradient as eluant to yield 0.66 g (98%) of 9 as a yellow oil. $^1$H NMR (400 MHz, $CDCl_3$): δ 3.39 (t, J=4.8 Hz, 2H), 3.47-3.51 (m, 2H), 3.60 (t, J=5.2 Hz, 2H), 3.63-3.69 (m, 22H), 3.88 (s, 1H), 7.07 (bs, 1H), $^{13}$C NMR (100.6 MHz, $CDCl_3$): δ 29.1, 40.0, 50.6, 69.4, 70.0, 70.4, 70.6-70.7, 165.8; MS ESI (m/z): $[M+H]^+$ calcd. for $C_{16}H_{32}BrO_7N_4$, 471.1, 473.1; found 471.0, 473.0

Example 9a

N-(20-azido-3,6,9,12,15,18-hexaoxaicosyl)-2-iodoacetamide (9a, $N_3$-$PEG_6$-IA)

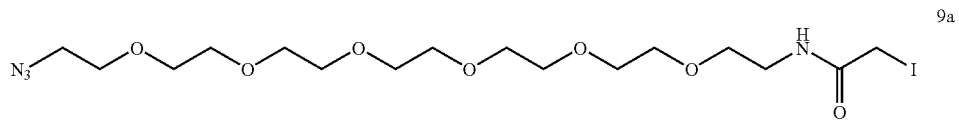 [SMILES: [N-]=[N+]=NCCOCCOCCOCCOCCOCCOCCNC(=O)CI]

A solution of 20-azido-3,6,9,12,15,18-hexaoxaicosan-1-amine ($NH_2$-$PEG_7$-$N_3$, 0.5 g, 1.43 mmol) and N-succinimidyl iodoacetate (0.4 g, 1.43 mmol) in DCM (5 mL) was stirred at room temperature for 2 h. The solvent was evaporated and the crude product was purified using flash chromatography on $SiO_2$ with a 0-100% DCM/MeOH gradient to yield 0.44 g (60%) of 9a as a yellow oil; MS ESI (m/z): $[M+H]^+$ calcd. for $C_{16}H_{32}IO_7N_4$, 519.34; found 519.4. $^1$H NMR (400 MHz, $CDCl_3$): δ 3.39 (t, J=5.2 Hz, 2H), 3.44-3.48 (m, 2H), 3.58 (t, J=5.2 Hz, 2H), 3.63-3.69 (m, 22H), 3.74 (s, 2H), 7.10 (bs, 1H). $^{13}$C NMR (100.6 MHz, $CDCl_3$): δ 26.0, 40.9, 51.3, 70.0, 70.6-71.3, 168.5 not clear

Example 10

3,6,9,12,15,18-hexaoxahenicos-20-yn-1-yl p-toluenesulfonate (10, propargyl-$PEG_6$-OTs)

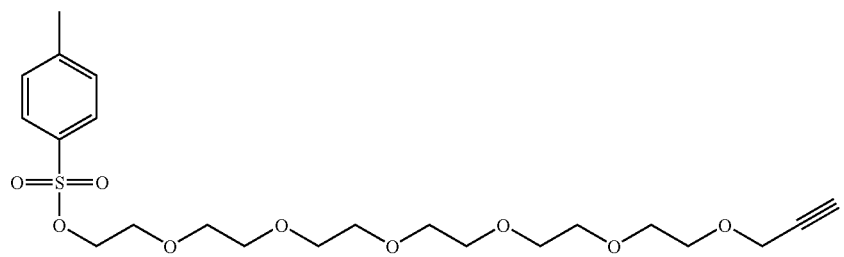

3,6,9,12,15,18-Hexaoxahenicos-20-yn-1-ol 1 and toluenesulfonyl chloride were reacted according to Example 3 to yield 0.5 g (47%) of 10 as a colorless oil. $^1$H NMR (400 MHz, CDCl$_3$): δ 2.42 (t, J=2.4 Hz, 1H), 2.45 (s, 3H), 3.58-3.70 (m, 22H), 4.16 (t, J=5.0 Hz, 2H), 4.20 (d, J=2.4 Hz, 2H), 7.34 (d, J=8.0 Hz, 2H), 7.80 (d, J=8 Hz, 2H); $^{13}$C NMR (100.6 MHz, CDCl$_3$): δ 21.6, 58.4, 68.7, 69.1, 70.4-70.7, 74.5, 79.5, 128.0, 129.8, 133.1, 144.7; MS ESI (m/z): [M+H]$^+$ calcd. for C$_{22}$H$_{35}$O$_9$S, 475.19; found 475.2.

Example 11

3,6-dioxanon-8-yn-1-ol (11, propargyl-PEG$_2$-OH)

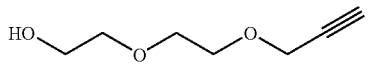

11

Diethylene glycol (3.0 g, 28.1 mmol) and propargyl bromide were reacted according to Example 1 to yield 1.2 g (30%) of 11 as a colorless oil. $^1$H NMR (400 MHz, CDCl$_3$): δ 2.38 (bs, 1H), 2.46 (t, J=2.4 Hz, 1H), 3.62 (t, J=4 Hz, 2H), 3.71-3.75 (m, 6H), 4.22 (d, J=2.4 Hz, 2H); MS ESI (m/z): [M+H]$^+$ calcd. for C$_7$H$_{13}$O$_3$, 145.08; found 145.3.

Example 12

3,6-dioxanon-8-yn-1-yl p-toluenesulfonate (12, propargyl-PEG$_2$-OTs)

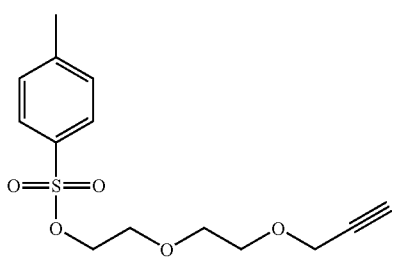

12

3,6-Dioxanon-8-yn-1-ol 11 (1.2 g, 8.3 mmol) and toluenesulfonyl chloride were reacted according to Example 3 to yield 1.7 g (68%) of 12 as a colorless oil. $^1$H NMR (400 MHz, CDCl$_3$): δ 2.44 (t, J=2.4 Hz, 1H), 2.45 (s, 3H), 3.60-3.65 (m, 4H), 3.70 (t, J=4.8 Hz, 2H), 4.15-4.18 (m, 4H), 7.35 (d, J=8.0 Hz, 2H), 7.80 (d, J=8 Hz, 2H); $^{13}$C NMR (100.6 MHz, CDCl$_3$): δ 21.6, 58.4, 68.7, 69.0, 69.2, 70.6, 74.6, 79.5, 128.0, 129.8, 133.1, 144.8; MS ESI (m/z): [M+H]$^+$ calcd. for C$_{14}$H$_{19}$O$_5$S, 299.09; found 299.1.

Example 13

Radiochemical Synthesis of [$^{18}$F]FPEGNHS 13

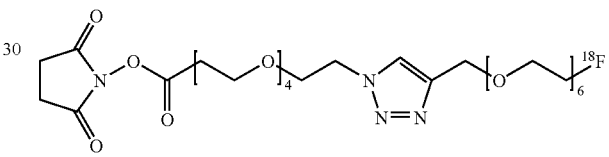

13

[$^{18}$F]Fluoride was eluted from T&R cartridge into a 4 mL v-vial using 10 μL 1.3 M TBAHCO$_3$ (tetra-n-butylammonium bicarbonate) in 0.6 mL of acetonitrile/water 1:1 (v/v). Water was azeotropically removed by microwave heating at 60 W, 120° C. under a stream of argon (600 ccm) followed by the addition of anhydrous acetonitrile (4×0.7 mL). 3,6,9,12,15,18-Hexaoxahenicos-20-yn-1-yl p-toluenesulfonate (propargyl-PEG$_6$-OTs) 10 (2 mg, 4.2 μmol) dissolved in acetonitrile (0.6 mL) was added and the mixture was microwave heated in a septum-sealed vessel at 40 W, 120° C. for 3 min. to give [$^{18}$F] 1-fluoro-3,6,9,12,15,18-hexaoxahenicos-20-yne:

[$^{18}$F] 1-fluoro-3,6,9,12,15,18-hexaoxahenicos-20-yne was evaporated to near dryness (no alumina treatment required), after which 4 mg (10.0 µmol) of N$_3$-PEG$_4$-NHS (Quanta Biodesign Ltd.) dissolved in acetonitrile (0.1 mL) was added. Next, a freshly prepared mixture of Cu(MeCN)$_4$PF$_6$ (3 mg, 8 µmol), TBTA (4.3 mg, 8 µmol), and 25 µL 2,6-lutidine in acetonitrile (0.2 mL) was added. The resulting light yellow solution was stirred for 10 min at room temperature, concentrated to 100 µL, diluted with H$_2$O with 0.1% TFA (1 mL), and delivered to the HPLC loop for purification. The crude product was purified by semi-preparative HPLC (system B) with a retention time of 15 min. The collected fraction was promptly diluted to 20 mL with H$_2$O, loaded on a Phenomenex Strata-X 60 mg SPE cartridge, the product trapped on the cartridge was rinsed with H$_2$O (10 mL), flushed with air, eluted with acetonitrile (0.5 mL) into a 1 mL v-vial, and evaporated at 30° C. to near dryness with 600 ccm argon to give [$^{18}$F]FPEGNHS 13.

Example 14

Direct $^{18}$F-Labeling of Propargyl-Modified 4D5ThioFab by CuAAC

A five-fold excess of 1-(3,6,9,12,15,18-hexaoxahenicos-20-yn-1-yl)-2,5-pyrroledione 2 (0.4 mg, 1 µmol) was added to 4D5ThioFab (10 mg, 0.2 µmol, 5 mg/mL, 50 mM sodium phosphate pH 7.2) and incubated for 1 hour at 37° C. The solution was adjusted to pH 4-5 with 10% acetic acid and purified by cation ion exchange chromatography on a HiTrap SP FF column (GE Healthcare) with 50 mM Tris buffer pH 8 with 100 mM sodium chloride. An aliquot of the recovered propargyl-modified 4D5ThioFab (100 ug) was added to dried [$^{18}$F] 23-azido-1-fluoro-3,6,9,12,15,18,21-heptaoxatricosane 4 followed by the addition of 1.2 mg BPDS in degassed buffer (250 uL Tris pH 8) and 0.26 mg Cu(MeCN)$_4$PF$_6$ in 20 uL acetonitrile. Atmospheric oxygen was excluded from the reaction system with Argon. However, the reaction shifted from dark brown to colorless over 10 min indicating that the reaction was quenched by oxygen and that more rigorous degassing conditions are required.

Example 15

Animal Models

Beige nude XID mice of age 6-8 weeks were obtained from Harlan Sprague Dawley (Livermore, Calif.). Three days prior to cell inoculation, the mice were implanted (s. c., left flank) with 0.36 mg 60-day sustained release 17β-estradiol pellets (Innovative Research of America) to maintain serum estrogen level. Mice were inoculated in the mammary fat pad with 5×10$^6$ BT474M1 cells, a subclone of BT474 (obtained from California Pacific Medical Center), in 50% phenol red-free matrigel. Animal care and treatment followed protocols approved by Genentech's Institutional Animal Care and Use Committee which is accredited by the Association for Assessment and Accreditation of Laboratory Animal Care (AAALAC)

Example 16

17-AAG Formulation and Administration

Egg-phospholipid (0.5 g) in DCM (5 mL) was transferred into 500 mL round bottom flask, the solvent evaporated and the residue was stored at the reduced pressure for 16 hours. The 5% (m/v) solution of dextrose (25 mL) was added to the dried phospholipids and the mixture was sonicated for 60 minutes at room temperature to obtain milky emulsion. 17-AAG (25 mg) was dissolved in DMSO (1 mL) of which an aliquot (0.25 mL) was mixed with the egg-phospholipid emulsion (4.8 mL) and sonicated at room temperature for 15 minutes. The resulting emulsion was administered with 30 minutes of preparation by intraperitoneal injection in three 1 mL doses (50 mg/kg each) over a 24 hour period as described previously (Smith-Jones et al (2006) J Nucl Med 47:793-6; Smith-Jones et al (2004) Nat Biotechnol 22:701-6). 17-AAG is 17-N-allylamino-17-demethoxygeldanamycin, a substance being studied in the treatment of cancer, specific young patients with certain types of leukemia or solid tumors. 17-AAG is also named as: [(3S,5S,6R,7S,8E,10R,11S,12E,14E)-21-(allylamino)-6-hydroxy-5,11-dimethoxy-3,7,9,15-tetramethyl-16,20,22-trioxo-17-azabicyclo[16.3.1]docosa-8,12,14,18,21-pentaen-10-yl] carbamate (CAS Reg. No. 75747-14-7).

Example 17

MicroPET Imaging

Mice were anesthetized with 3% sevoflurane and inoculated i.v. via the tail vein catheter with 0.3-0.4 mCi of $^{18}$F-Thio4D5Fab in isotonic solution (50-100 µL). The animals were allowed to recover on a heated blanket until ambulatory and then returned to the cage. After 2 hours of conscious uptake the animals were anesthetized with 3% sevoflurane and placed head-first, prone position on the scanner bed. Body temperature was measured by a rectal probe and maintained by warm air. Dynamic 60 min scans were acquired. Full body image reconstructions were obtained using maximum a posteriori algorithm (MAP) and maximum intensity projections (MIPs) were created with ASIPro software (CTI Molecular Imaging). MAP reconstructed images were used to obtain quantitative activity levels in each organ of interest using ASIPro software (CTI Molecular Imaging).

Statistical analysis: The graphs were constructed with R software version 2.4.1 (R Foundation for Statistical Computing, Vienna, Austria). Statistical significance was determined using a two-tailed Student's t-test and P values of less than 0.05 were considered significant; data are presented as mean±s.e.m. if not stated otherwise.

We claim:

1. A method of labelling an antibody comprising reacting a labelling reagent selected from:

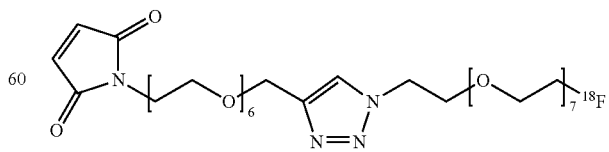

and an antibody, wherein the antibody comprises a free cysteine thiol, and
whereby a labelled antibody is formed.

2. The method of claim 1 wherein the antibody is selected from the group consisting of a monoclonal antibody, a bispecific antibody, a murine antibody, a chimeric antibody, a human antibody, and a humanized antibody.

3. The method of claim 2 wherein the antibody is a Fab fragment.

4. The method of claim 3 wherein the Fab fragment is 4D5ThioFab.

5. A process for making a labelling reagent having the formula:

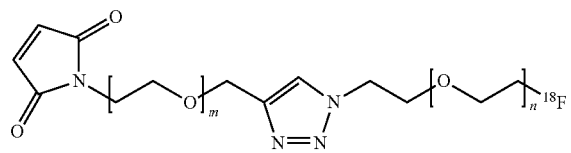

comprising reacting a maleimide-PEG-alkyne reagent having the formula:

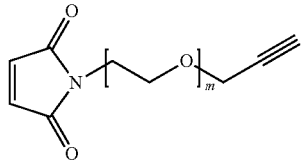

with an $^{18}$F-PEG-azide reagent having the formula:

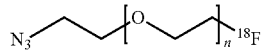

in the presence of a copper catalyst,
wherein m is 6 and n is 7;
whereby the labelling reagent is formed.

* * * * *